(12) United States Patent
Yamaya

(10) Patent No.: US 10,905,312 B2
(45) Date of Patent: Feb. 2, 2021

(54) ENDOSCOPE SYSTEM

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 336 days.

(21) Appl. No.: 16/007,387

(22) Filed: Jun. 13, 2018

(65) Prior Publication Data

US 2018/0289245 A1 Oct. 11, 2018

Related U.S. Application Data

(63) Continuation of application No. PCT/JP2017/000040, filed on Jan. 4, 2017.

(30) Foreign Application Priority Data

Jan. 14, 2016 (JP) .................................. 2016-005544

(51) Int. Cl.
*A61B 1/00* (2006.01)
*G02B 23/24* (2006.01)
(Continued)

(52) U.S. Cl.
CPC ........ *A61B 1/00135* (2013.01); *A61B 1/0011* (2013.01); *A61B 1/0057* (2013.01);
(Continued)

(58) Field of Classification Search
None
See application file for complete search history.

(56) References Cited

U.S. PATENT DOCUMENTS 5,685,823 A * 11/1997 Ito ..................... A61B 1/00091
600/121

FOREIGN PATENT DOCUMENTS

JP H04-314439 A 11/1992
JP 2002-204774 A 7/2002
(Continued)

OTHER PUBLICATIONS

English translation of International Preliminary Report on Patentability dated Jul. 26, 2018 together with the Written Opinion received in related International Application No. PCT/JP2017/000040.

(Continued)

*Primary Examiner* — Timothy J Neal
(74) *Attorney, Agent, or Firm* — Scully, Scott, Murphy & Presser, P.C.

(57) ABSTRACT

An endoscope system includes, an insertion section; a distal structure portion provided at a distal end of the insertion section; a pivot base; an elongated pulling member connected to the pivot base; a tubular elastic member configured to cover the pulling member; a cylindrical cover configured to be attached to the distal structure portion, and including an opening portion; a cover removing tool configured to be capable of pushing an edge of the opening portion, in a state in which the cover removing tool is engaged with the cover; and a projection provided on the cover removing tool, the projection being configured to come in contact with the edge of the opening portion at a position apart from a position of the one end of the elastic member.

8 Claims, 19 Drawing Sheets

(51) Int. Cl.
*A61B 1/005* (2006.01)
*A61B 1/018* (2006.01)
(52) U.S. Cl.
CPC ...... *A61B 1/00089* (2013.01); *A61B 1/00098* (2013.01); *A61B 1/00101* (2013.01); *G02B 23/2476* (2013.01); *A61B 1/018* (2013.01)

(56) References Cited

FOREIGN PATENT DOCUMENTS

| JP | 2003-102668 A | 4/2003 |
| JP | 2004-181030 A | 7/2004 |
| JP | 2010-253061 A | 11/2010 |

OTHER PUBLICATIONS

International Search Report dated Mar. 21, 2017 issued in PCT/JP2017/000040.

* cited by examiner

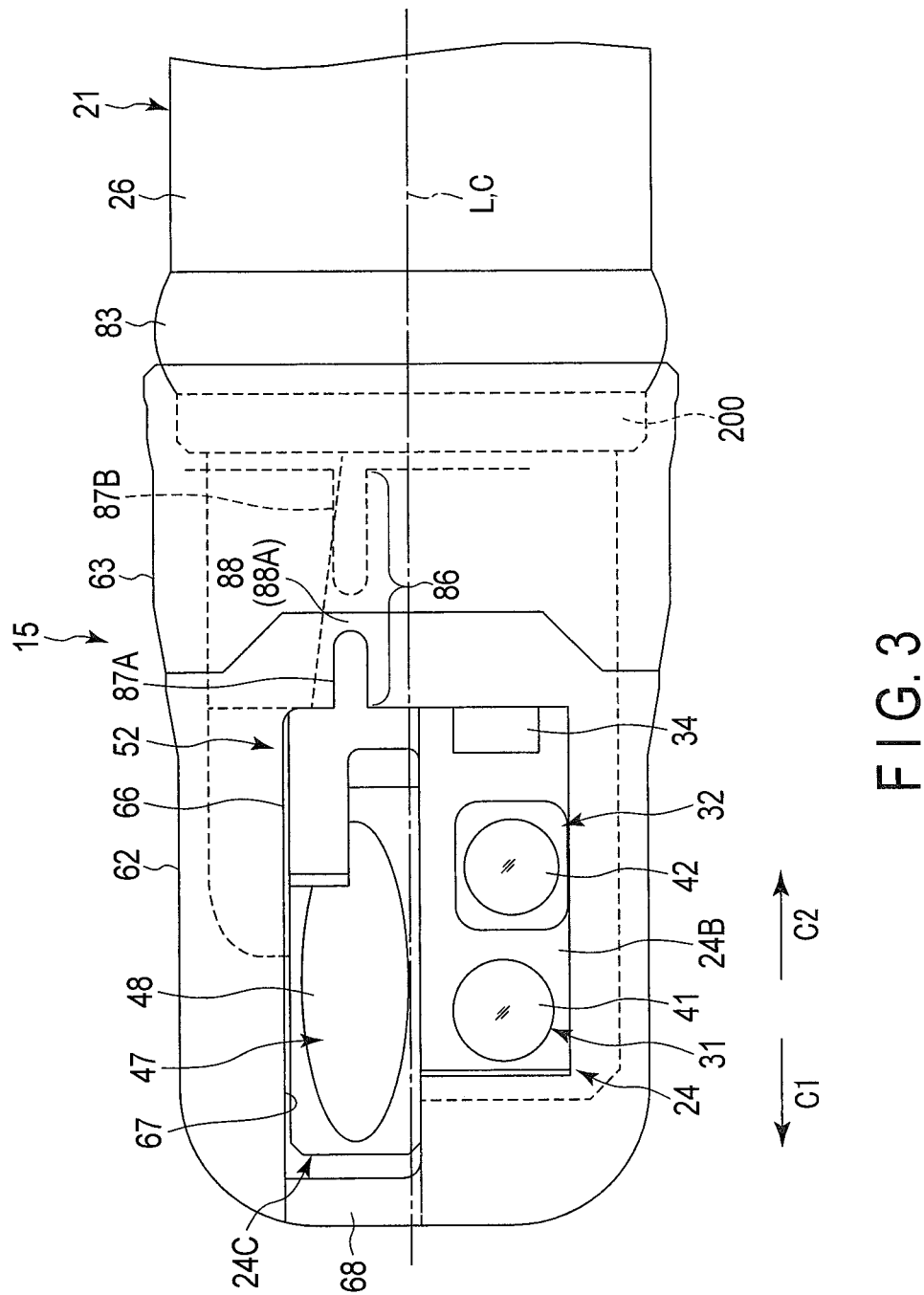
F I G. 3

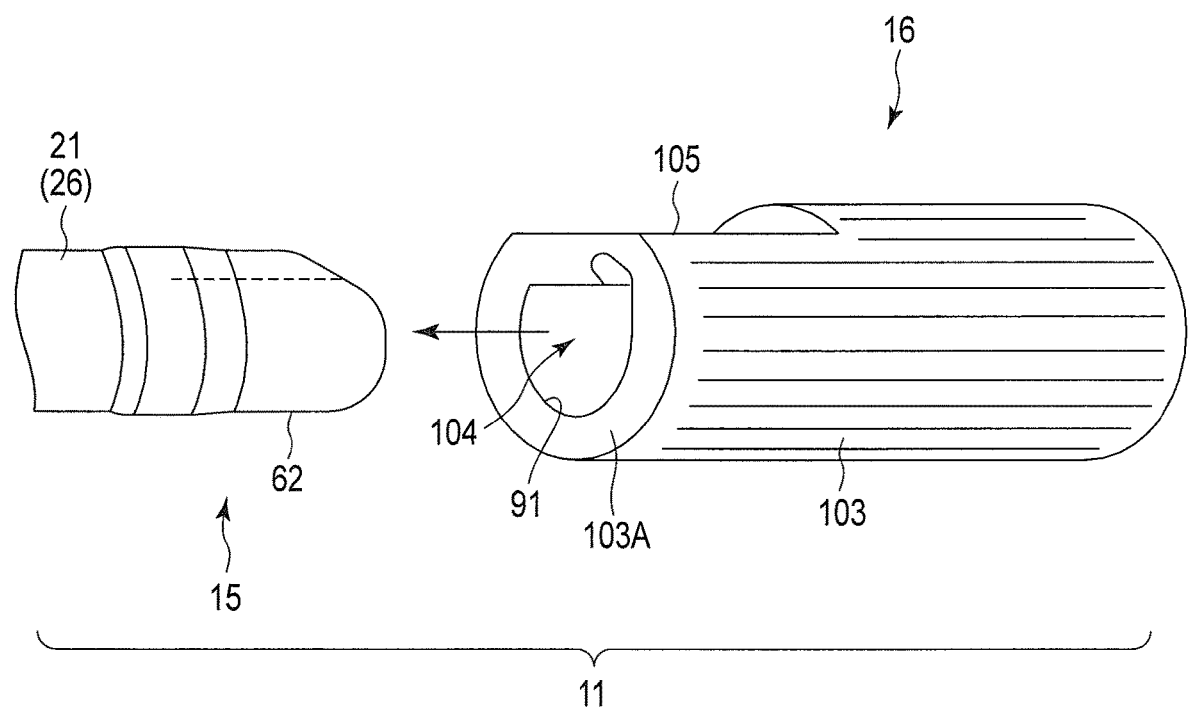
F I G. 11

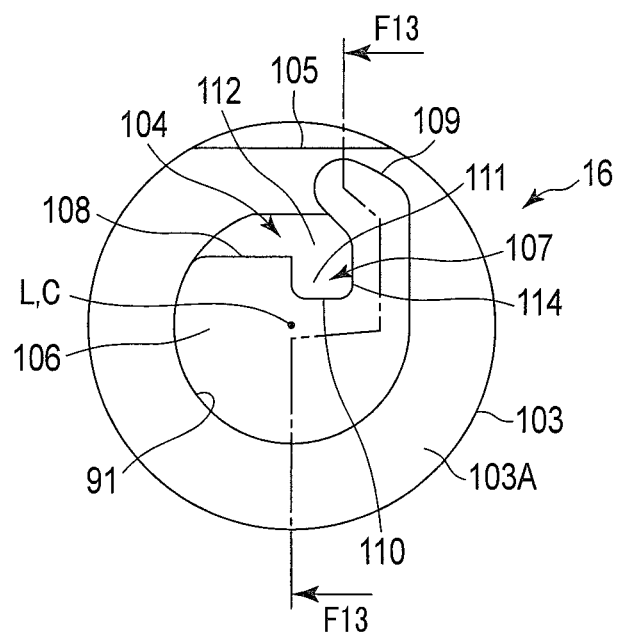
F I G. 12
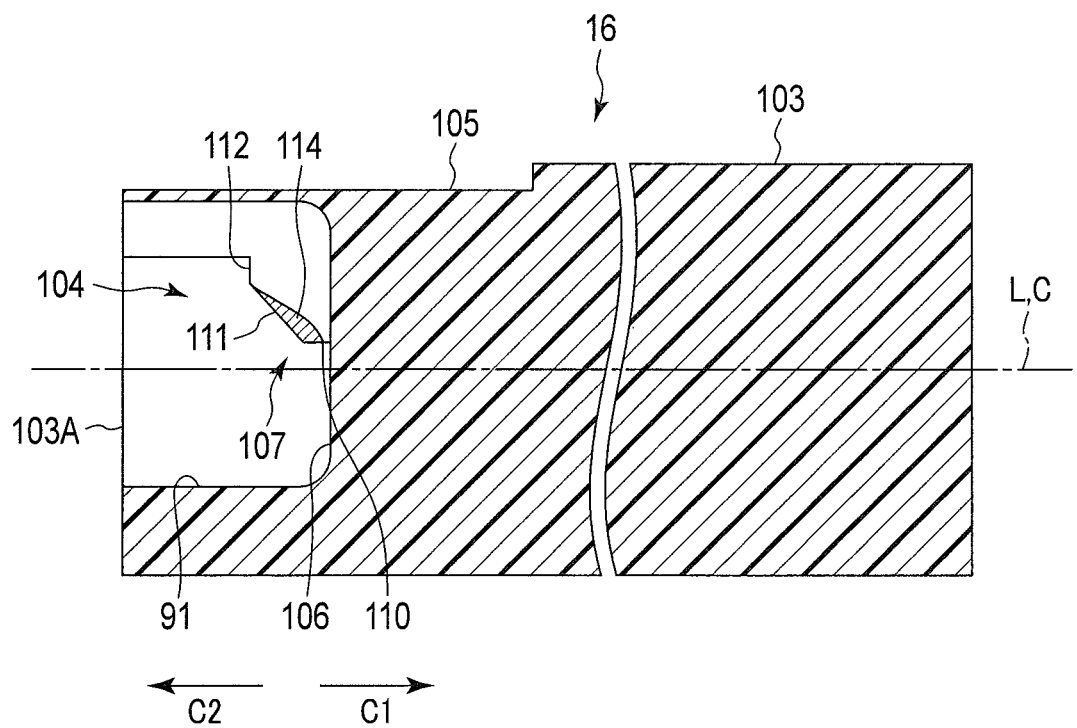
F I G. 13

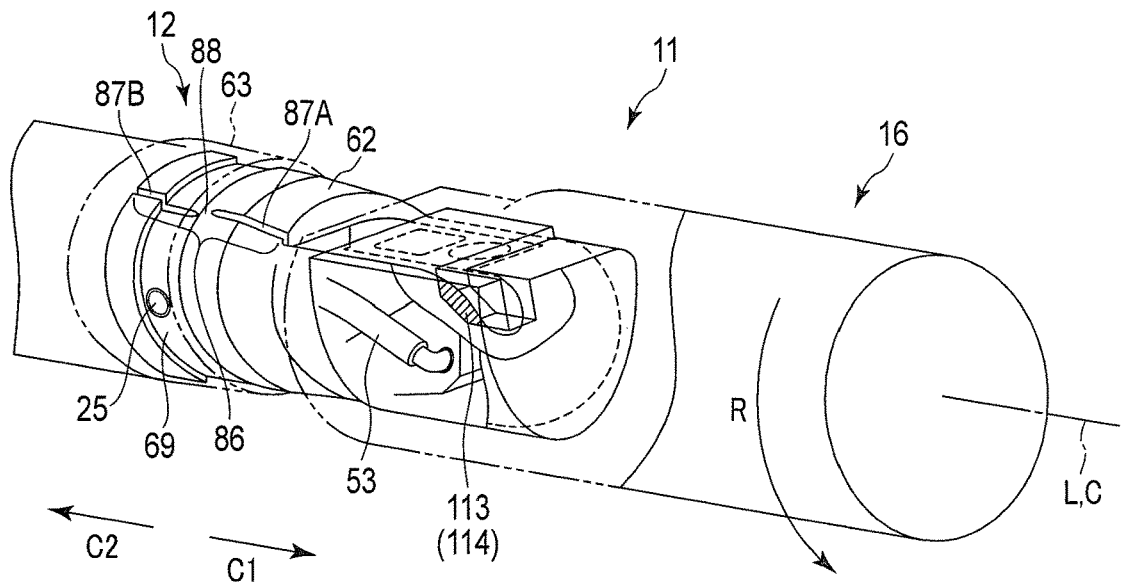
F I G. 15
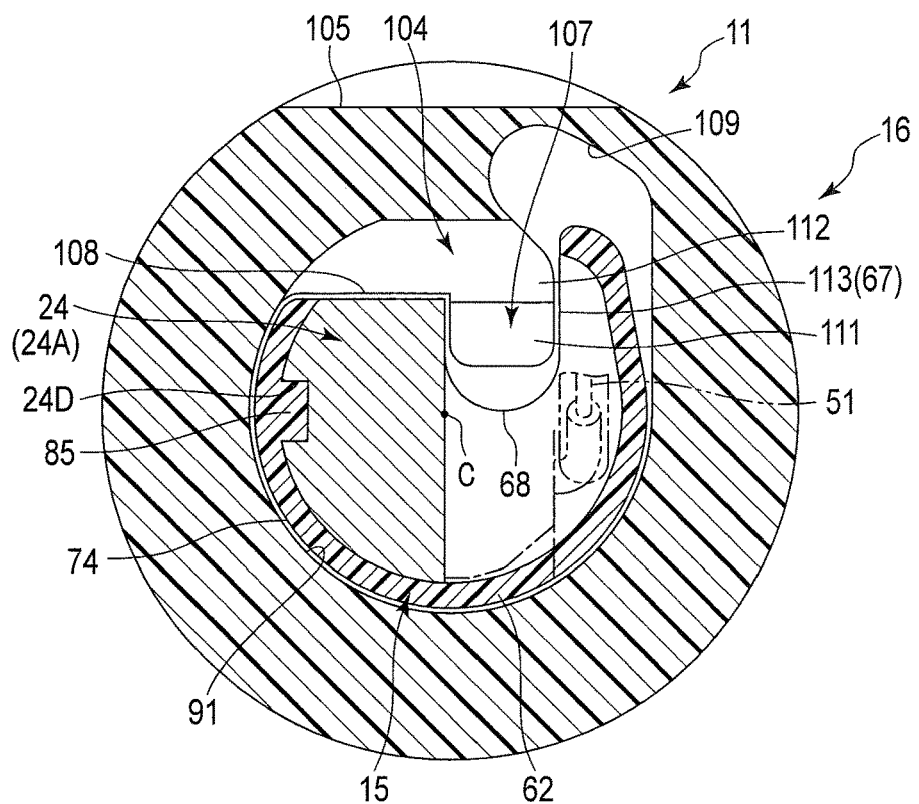
F I G. 16

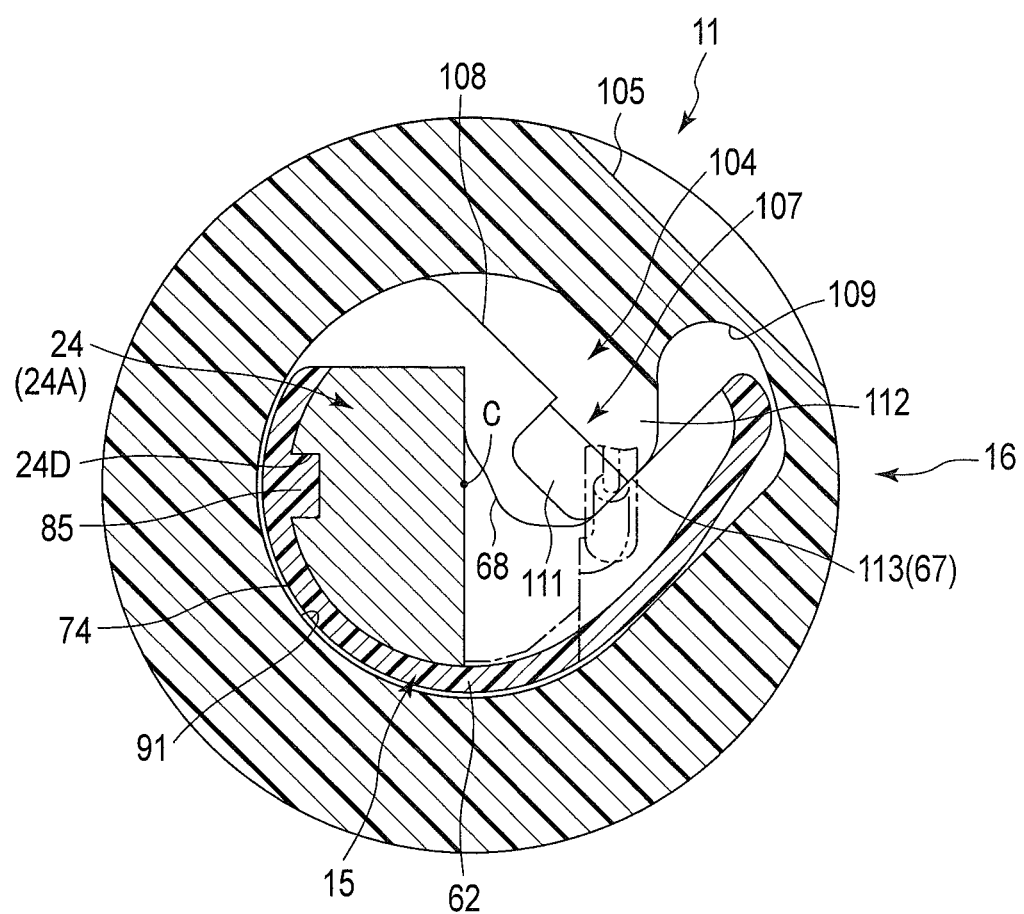
F I G. 17

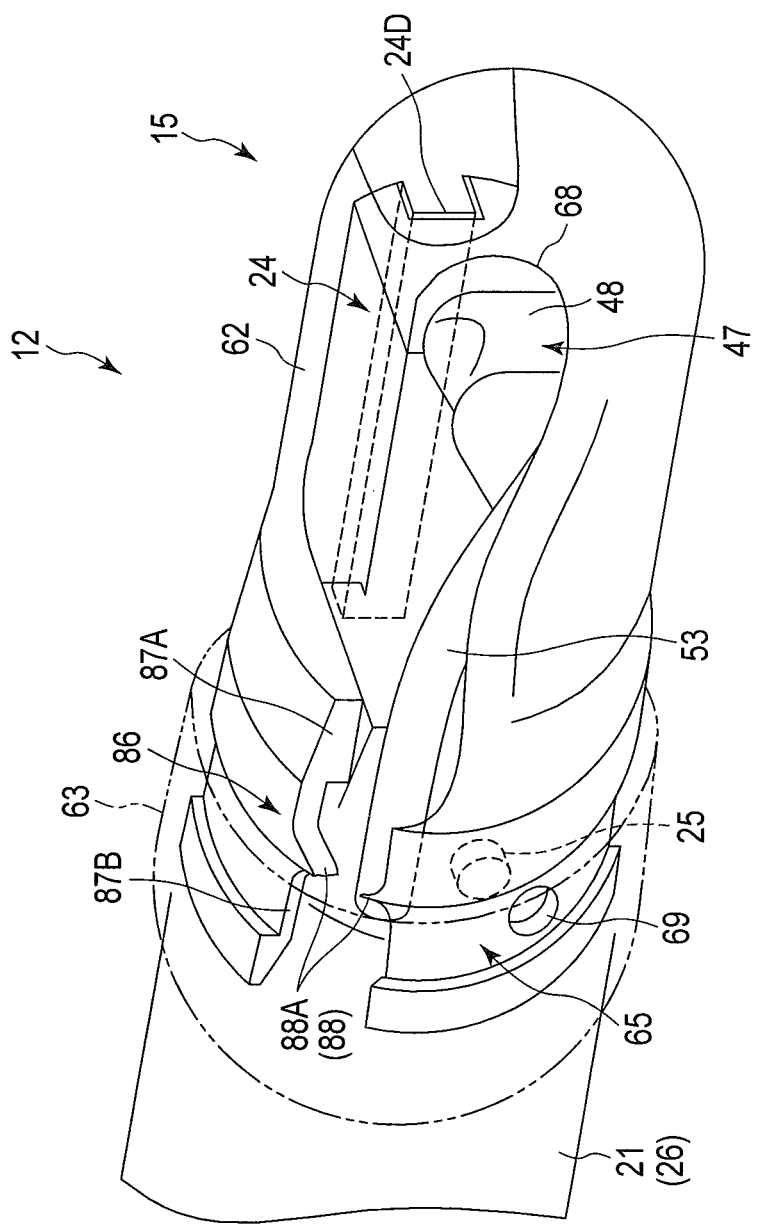
F I G. 18

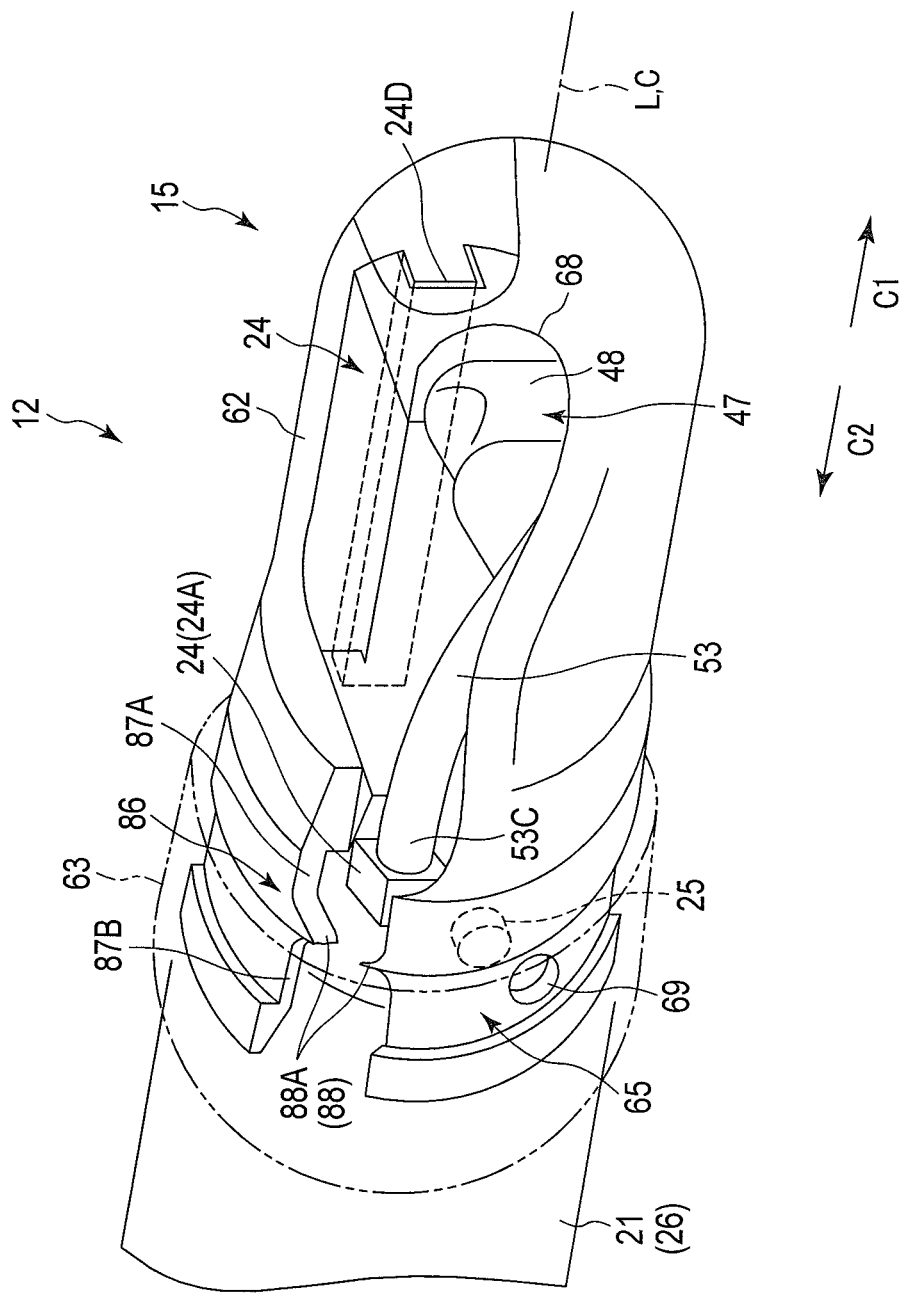
F I G. 20

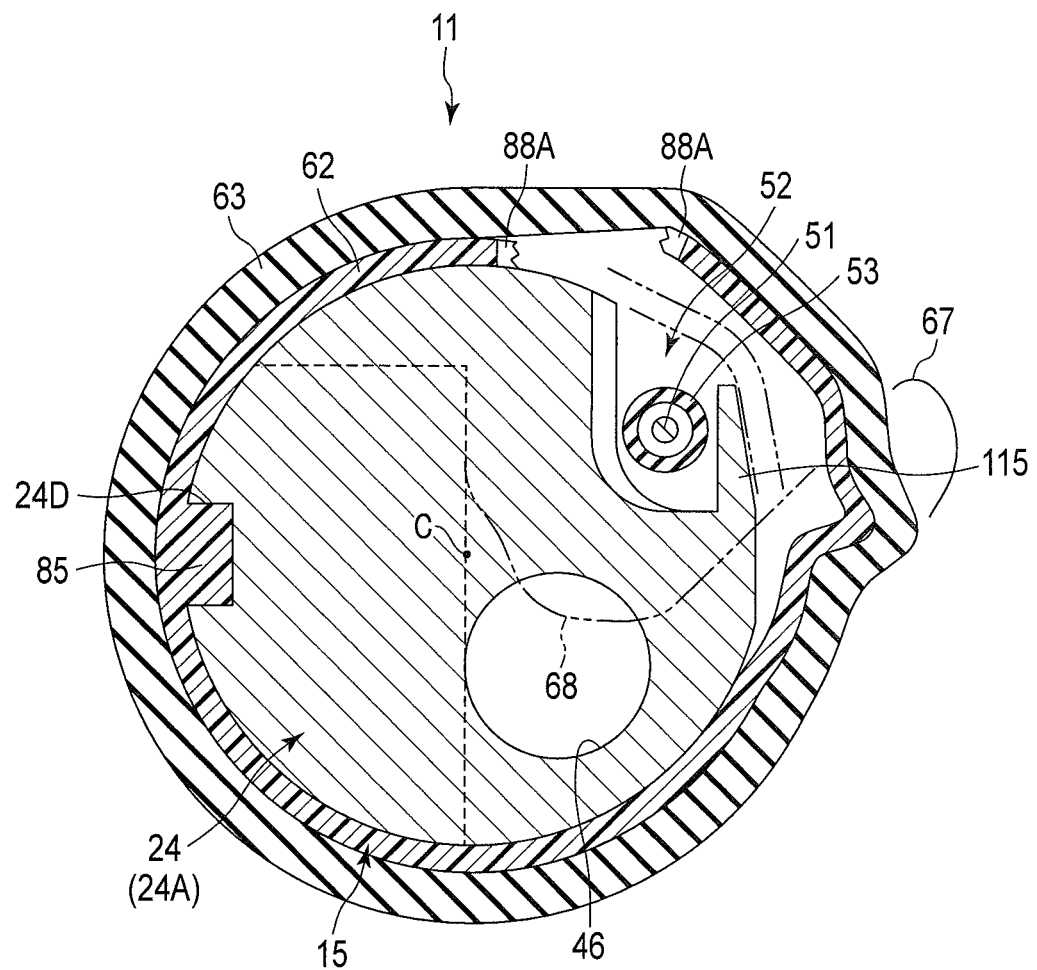
F I G. 21

ENDOSCOPE SYSTEM

CROSS-REFERENCE TO RELATED APPLICATIONS

This application is a Continuation Application of PCT Application No. PCT/JP2017/000040, filed Jan. 4, 2017 and based upon and claiming the benefit of priority from prior Japanese Patent Application No. 2016-005544, filed Jan. 14, 2016, the entire contents of all of which are incorporated herein by reference.

BACKGROUND OF THE INVENTION

1. Field of the Invention

The present invention relates to an endoscope system including a cover which is attached to a distal structure portion of an insertion section.

2. Description of the Related Art

For example, Jpn. Pat. Appln. KOKAI Publication No. 2003-102668 discloses a cover which is attached to a distal structure portion of an insertion section of an endoscope. This cover is removed by being ripped along a groove formed from a proximal edge portion toward a distal side thereof. When the cover is removed from the distal structure portion, work for ripping the cover from the proximal edge portion toward the distal side thereof is performed by a tool or fingers.

BRIEF SUMMARY OF THE INVENTION

An endoscope system comprising: an insertion section which is inserted into a lumen cavity along a longitudinal axis; a distal structure portion provided at a distal end of the insertion section; a pivot base configured to pivotally move a treatment instrument at the distal end of the insertion section; an elongated pulling member connected to the pivot base in the distal structure portion, and configured to remotely operate the pivot base;

a tubular elastic member configured to cover the pulling member, the elastic member including one end water-tightly connected to a distal side of the pulling member or the pivot base, and the other end water-tightly connected to the distal structure portion; a cylindrical cover configured to be attached to the distal structure portion, and including an opening portion in a peripheral surface thereof; a cover removing tool configured to be capable of pushing an edge of the opening portion, in a state in which the cover removing tool is engaged with the cover; and a projection provided on the cover removing tool, the projection being configured to come in contact with the edge of the opening portion at a position apart from a position of the one end of the elastic member in a direction of the longitudinal axis, in a state in which the cover removing tool is engaged with the cover.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is a plan view, as viewed in a direction directly facing a planar part of the distal structure portion illustrated in FIG. 2.

FIG. 11 is a perspective view illustrating a step of attaching the cover removing tool, which is included in the endoscope system, to the cover of the endoscope.

FIG. 12 is a front view of the cover removing tool shown in FIG. 11, as viewed from one end side thereof.

FIG. 13 is a cross-sectional view taken along line F13-F13 of the cover removing tool shown in FIG. 12.

FIG. 15 is a perspective view illustrating a step of rotating the cover removing tool in an R direction relative to the cover (endoscope) shown in FIG. 14.

FIG. 16 is a cross-sectional view taken along line F16-F16 in FIG. 8, illustrating the cover, distal structure portion and cover removing tool.

FIG. 17 is a cross-sectional view illustrating a state of the cover, distal structure portion and cover removing tool shown in FIG. 16, after the cover removing tool was rotated by a predetermined angle relative to the distal structure portion.

FIG. 18 is a perspective view illustrating a state in which a fragile portion (coupling portion) of the cover body was broken by the rotation of the cover removing tool.

FIG. 20 is a perspective view illustrating a state in which a coupling portion was broken by rotating the cover removing tool by a predetermined angle in an endoscope system according to a first modification of the embodiment.

FIG. 21 is a cross-sectional view taken along line F19-F19 in FIG. 8, FIG. 21 illustrating a partition wall of the distal structure portion, the wire and the elastic member in an endoscope system according to a second modification of the embodiment, in a state after the coupling portion was broken by rotating the cover removing tool by a predetermined angle.

DETAILED DESCRIPTION OF THE INVENTION

Hereinafter, an embodiment for implementing the present invention will be described with reference to the accompanying drawings.

Figure 1:
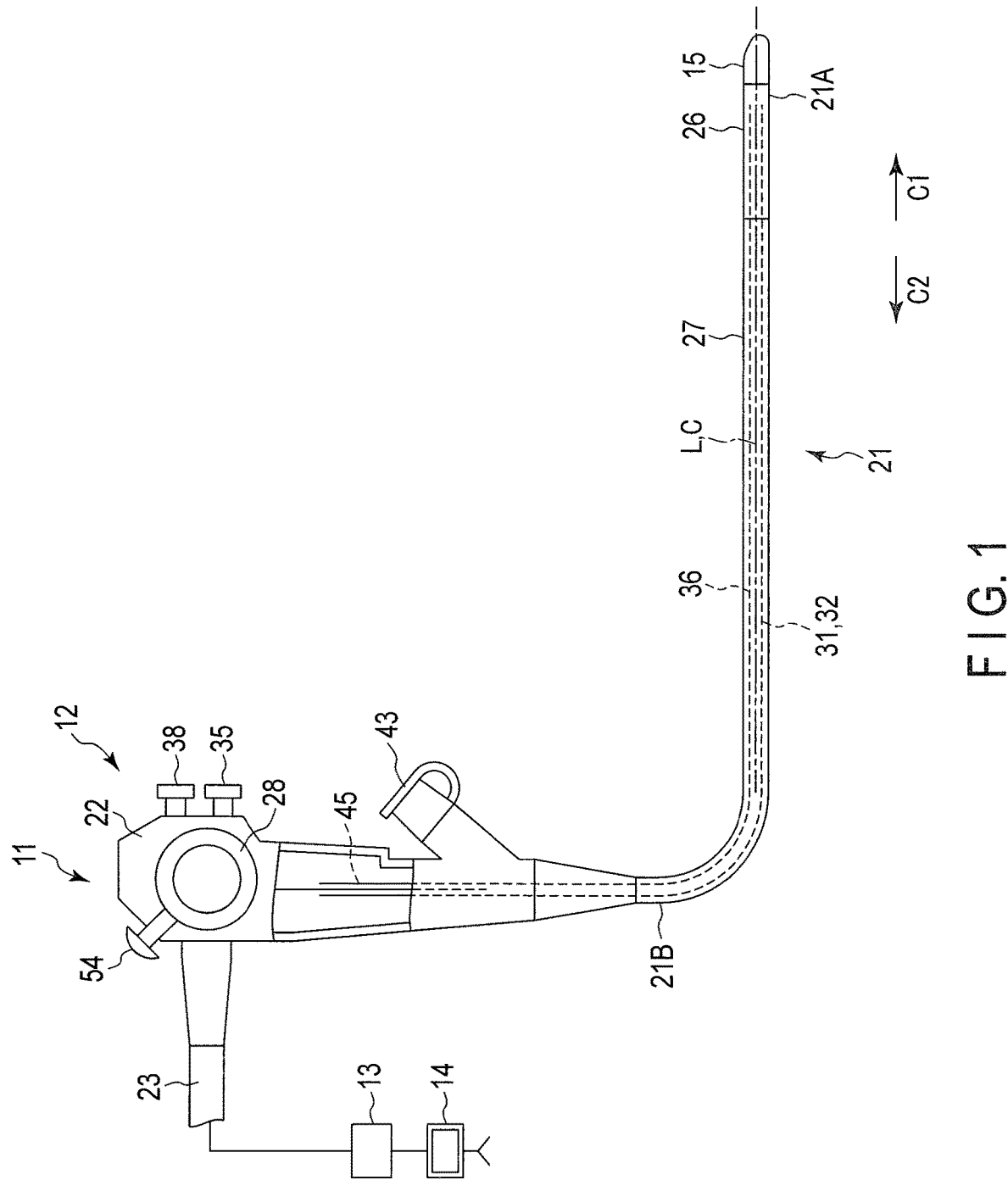
FIG. 1 is a schematic view illustrating an endoscope of an endoscope system according to an embodiment.

An endoscope of a first embodiment will be described with reference to FIG. 1 to FIG. 19. As illustrated in FIG. 1 and FIG. 11, an endoscope system 11 includes an endoscope 12; an endoscope controller 13 (image processing unit) which performs image processing, based on a subject image captured by the endoscope 12; a monitor 14 which displays video that is generated by the image processing in the endoscope controller 13; and a cover removing tool 16 for removing a cover 15 at a distal end of the endoscope 12.

Figure 2:
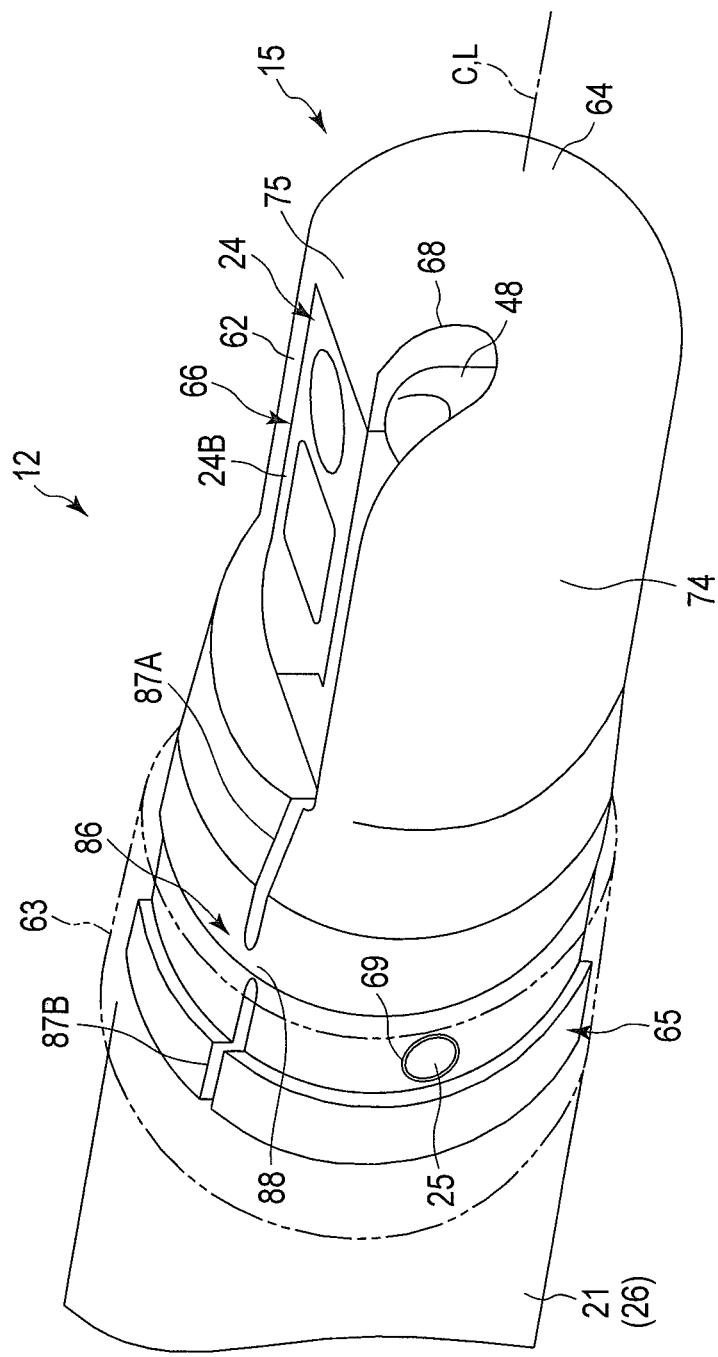
FIG. 2 is a schematic perspective view which schematically illustrates a distal structure portion of the endoscope illustrated in FIG. 1, and a cover which is attached to the distal structure portion.

As illustrated in FIG. 1 and FIG. 2, the endoscope 12 (insertion device) includes an insertion section 21 which is inserted into a tract such as a lumen cavity along a longitudinal axis L; the cover 15 (endoscope cover) which is attached to a distal end the insertion section 21; an operation section 22 which is grasped by a user; a universal cord 23 extending from the operation section 22; and a distal structure portion 24 provided at the distal end of the insertion section 21. Although details will be described later, the cover 15 is formed as a disposable type. The cover 15 is easily attachable to the distal structure portion 24 of the insertion section while the shape thereof is being maintained. However, the cover 15 is formed not to be easily detachable from the distal structure portion 24, for example, by an engaging pin 25 (to be described later) or the like.

As illustrated in FIG. 1, the insertion section 21 defines a longitudinal axis L by a distal end 21A and a proximal end 21B thereof. The insertion section 21 includes the distal structure portion 24, a bending portion 26 and a tube portion 27 in the named order from the distal end 21A toward the proximal end 21B. The tube portion 27 may be a flexible one which is a so-called flexible endoscope, or may be a so-called rigid endoscope which keeps a straight state and has resistance to bending. The bending portion 26 can be bent in a plurality of directions, for example, in two directions or four directions, by a knob 28 of the operation section 22 by a publicly known mechanism. Incidentally, in the embodiment to be described below, the description will be given by defining a distal direction side of the longitudinal axis L as C1, and by defining a proximal direction side opposite to the distal direction of the longitudinal axis L as C2. The distal structure portion 24 is provided at the distal end of the insertion section 21.

The endoscope 12 includes an illumination optical system 31, an observation optical system 32 and a treatment instrument insertion channel 36. Besides, although not illustrated, the endoscope 12 includes an air/water supply mechanism and a suction mechanism. The air/water supply mechanism includes a nozzle 34 (to be described) at a distal end thereof, and is operated by a first button 35 of the operation section 22. The suction mechanism communicates with the channel 36, and is operated by a second button 38 of the operation section 22.

The illumination optical system 31 and observation optical system 32 are inserted through the distal structure portion 24, bending portion 26 and tube portion 27 of the insertion section 21 of the endoscope 12, the operation section 22, and the universal cord 23. As illustrated in FIG. 3, the illumination optical system 31 includes an illumination window 41 in the distal structure portion 24. The observation optical system 32 includes an observation window in the distal structure portion 24.

Figure 8:
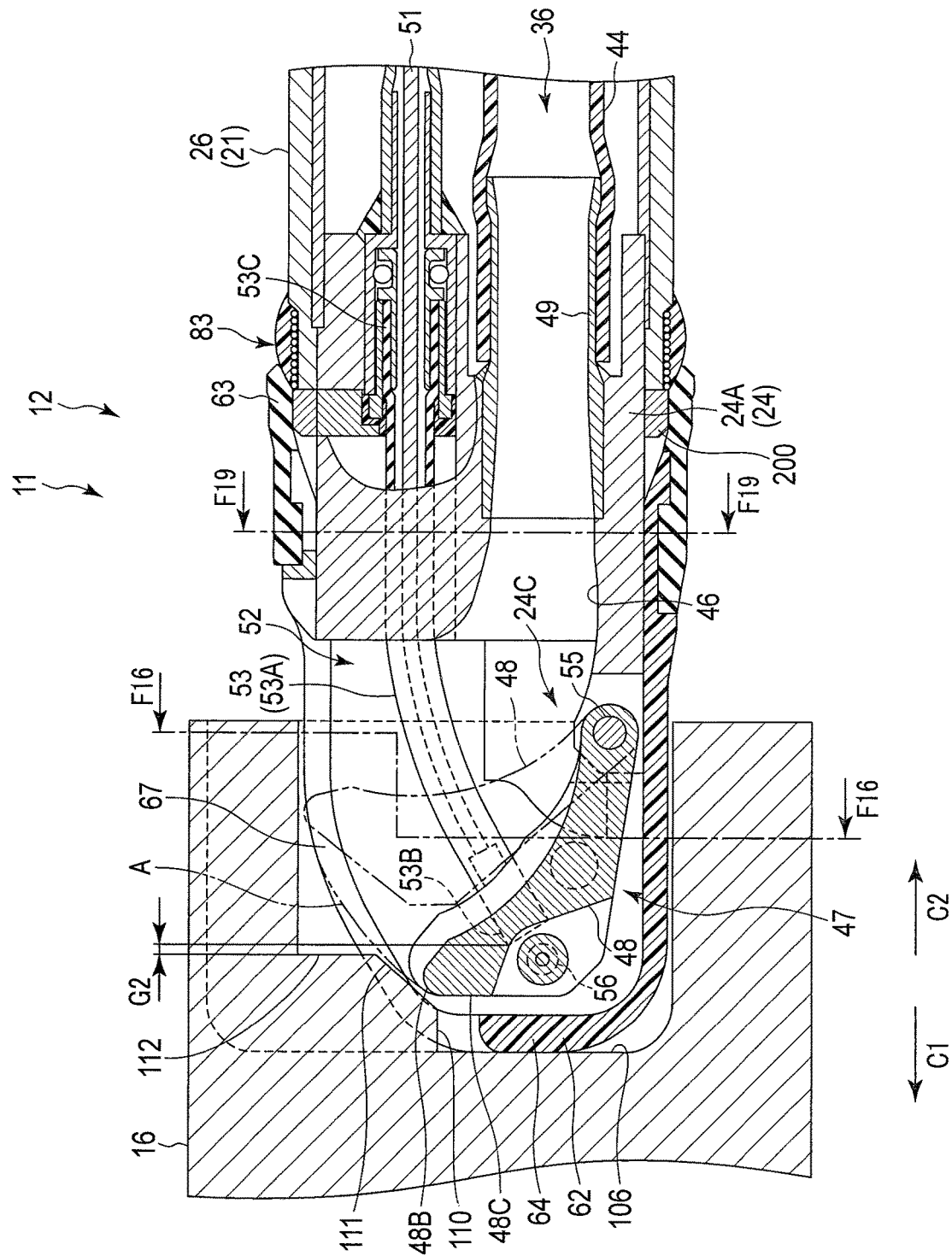
FIG. 8 is a cross-sectional view illustrating a state in which a cover removing tool is attached to the cover of the endoscope, FIG. 8 being taken by a plane along a longitudinal axis.

The channel 36 has a distal end opened in the distal structure portion 24 of the insertion section 21 of the endoscope 12. The channel 36 has a proximal end opened near a proximal portion of the tube portion 27 of the insertion section 21, or opened in the operation section 22. Here, as illustrated in FIG. 1, an opening (not shown) of the proximal end of the channel 36 is provided in the operation section 22, and a forceps tap 43 is detachably attached to this opening via a mouthpiece. As illustrated in FIG. 8, a distal end of a tube 44 of the channel 36 is fixed to the distal structure portion 24 via a mouthpiece 49. In the meantime, as illustrated in FIG. 1, the tube 44 of the channel 36 is branched into a publicly known suction conduit 45, for example, in the inside of the operation section 22. The suction conduit 45 is coupled to the second button 38. By a pressing operation of the second button 38, sucked matter is discharged from an opening portion 46 (to be described later) at the distal end of the channel 36 via the mouthpiece, tube 44, suction conduit 45 and universal cord 23.

In this embodiment, the distal structure portion 24 is formed as such a side-viewing type that the direction of observation is different from a direction along the longitudinal axis L of the insertion section 21. The endoscope 12 includes a pivot mechanism 47 which properly adjusts the direction of a treatment instrument (not shown) or the like, which is passed through the channel 36, thereby enabling observation within the view field.

Figure 5:
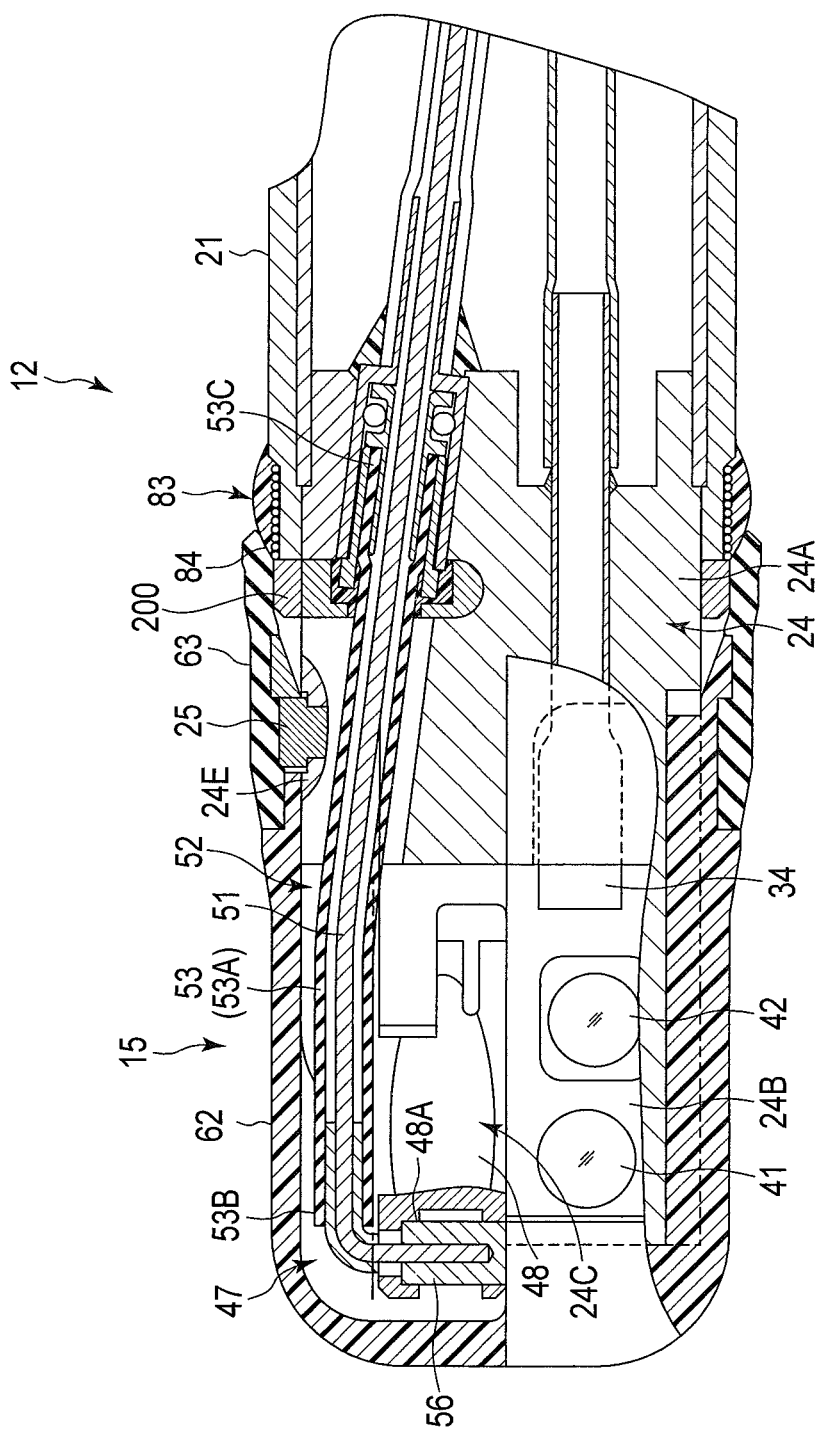
FIG. 5 is a partial cross-sectional view illustrating the distal structure portion illustrated in FIG. 2, the cover and a wire, FIG. 5 being taken by a plane along the wire.

The pivot mechanism 47 will be described in brief, since this pivot mechanism 47 is publicly known. The pivot mechanism 47 has a distal end in the distal structure portion 24 of the insertion section 21 of the endoscope 12, and has a proximal end in the operation section 22. As illustrated in FIG. 1, FIG. 8, etc., the pivot mechanism 47 includes, in the named order from the distal end toward the proximal end of the insertion section 21, a pivot base 48; an elongated (linear) wire 51 (pulling member); an elastic member 53 covering a part where the wire 51 is exposed in a wire moving section 52 (to be described later); and a lever 54. The pivot base 48 is supported on the distal structure portion 24 via a support pin 55, and can pivotally move the treatment instrument at the distal end of the insertion section 21. A distal end of the wire 51 is supported by the pivot base 48, and a proximal end of the wire 51 is supported by the lever 54. The wire 51 (pulling member) is connected to the pivot base 48 in a wire moving section 52 provided in the distal structure portion 24, and can remotely operate the pivot base 48. As illustrated in FIG. 5, an operating shaft portion 56, which is formed in an "L" shape, is provided at the distal end of the wire 51. The operating shaft portion 56 is fitted in a receiving portion 48A such that the operating shaft portion 56 is rotatable relative to the receiving portion 48A of the pivot base 48 and does not drop from the receiving portion 48A.

As illustrated in FIG. 5, the elastic member 53 is formed of a material, such as rubber, in a cylindrical shape (tubular shape). An exposed part of the wire 51 can be passed through the inside of the elastic member 53. The elastic member 53 includes an elastic member body 53A; one end 53B which is water-tightly fixed to the pivot base 48 side on the distal direction C1 side of the longitudinal axis L; and the other end 53C which is water-tightly fixed to the distal structure portion 24 on the proximal direction C2 side of the longitudinal axis L. The elastic member 53 can prevent entrance of liquid or gas into the inside thereof. The elastic member 53 prevents liquid or gas from entering the inside of the insertion section along the wire 51, to be more specific, the inside of the tube portion 27 of the insertion section 21. Specifically, both ends of the elastic member 53 are water-tightly connected to the pivot base 48 and the distal structure portion 24. Incidentally, it is preferable that the elastic member 53 is formed to have a certain length. Thereby, even when the wire 51 is advanced and retreated and the pivot mechanism 47 is repeatedly operated, the amount of extension and contraction per unit length of the elastic member 53 can be reduced, and the durability of the elastic member 53 can be improved.

Figure 6:
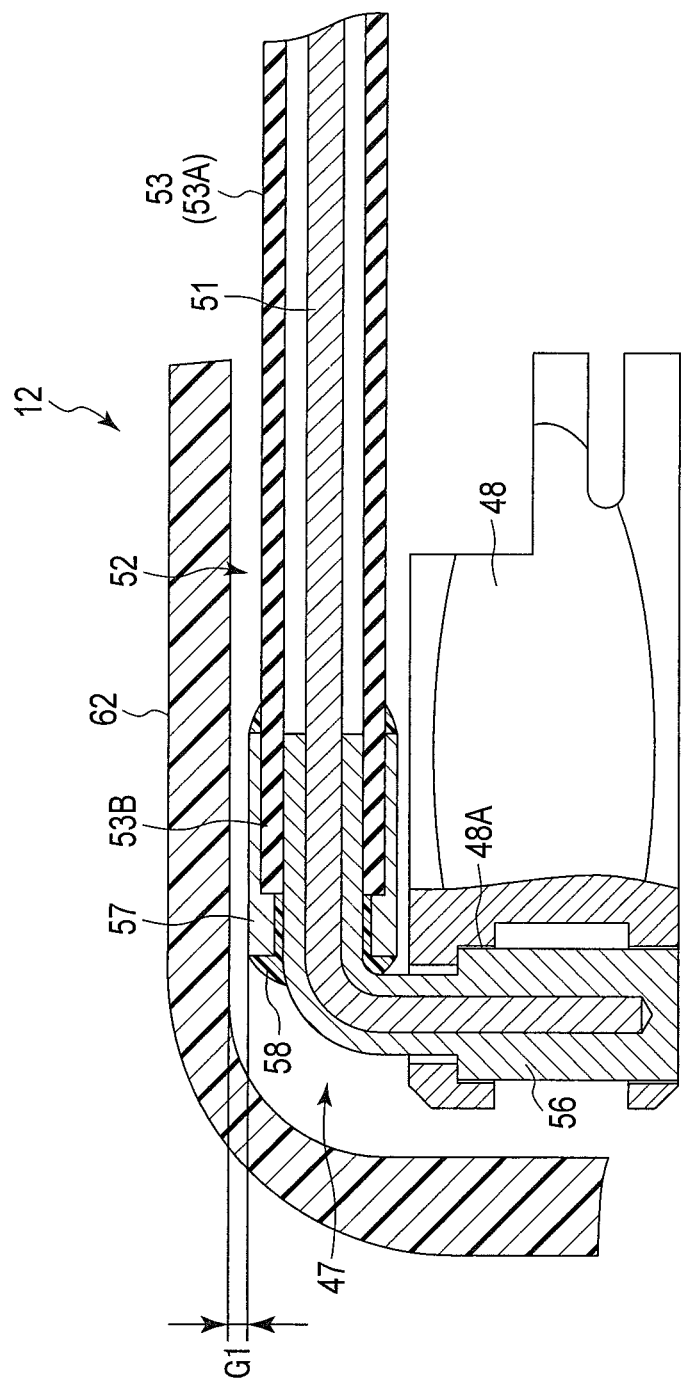
FIG. 6 is a cross-sectional view illustrating in detail a pivotal mechanism which is shown in FIG. 5, FIG. 6 illustrating the cover body, a pivot base of the pivotal mechanism, the wire, an elastic member, and a ring member.
Figure 7:
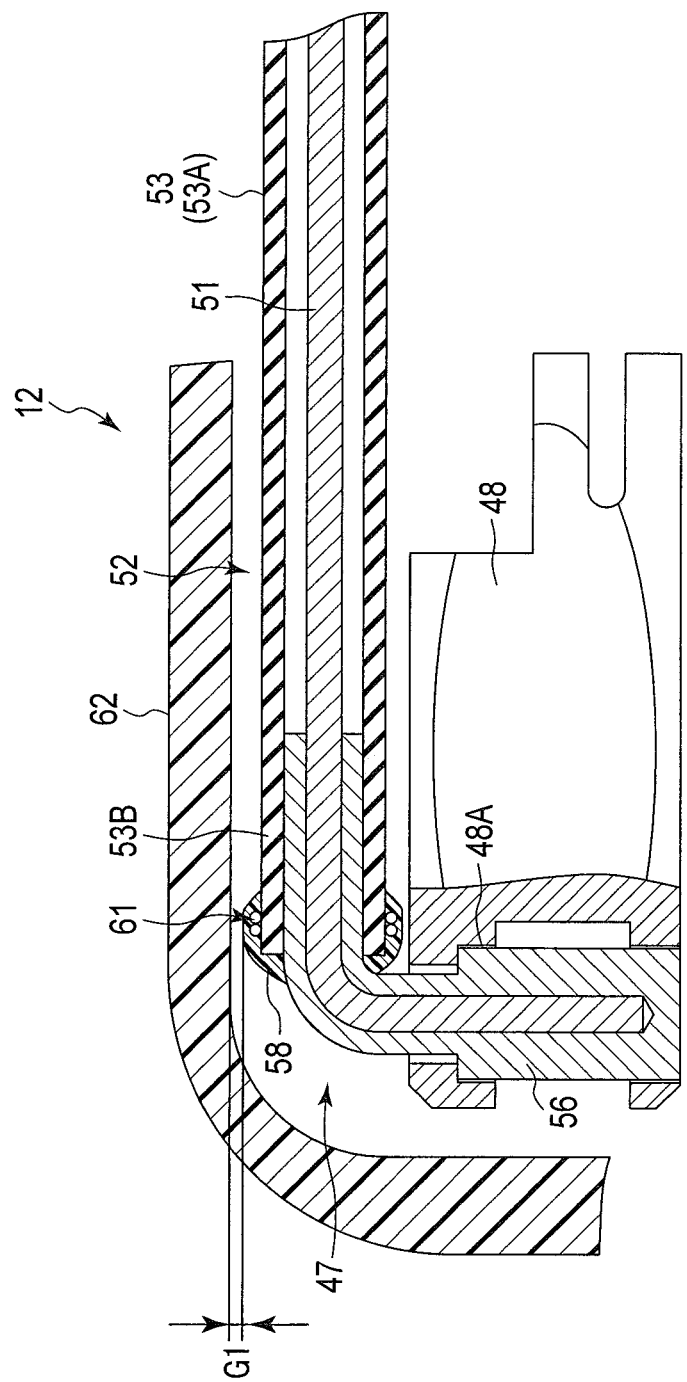
FIG. 7 is a cross-sectional view illustrating in detail another example of the pivotal mechanism which is shown in FIG. 5, FIG. 7 illustrating the cover body, the pivot base of the pivotal mechanism, the wire, the elastic member, and a bobbin structure.

As illustrated in FIG. 6, the one end 53B of the elastic member 53 is fixed to an end portion of the operational shaft portion 56, which projects from the pivot base 48, via a fixing ring member 57 and an adhesive 58. In addition, as illustrated in FIG. 7, the one end 53B of the elastic member 53 may be fixed by a bobbin structure 61 such that a string is wound around the periphery of the one end 53B and the adhesive 58 is applied from the upper side of the string. In each of the structures of FIG. 6 and FIG. 7, a gap G1 is provided in a direction crossing the longitudinal axis L between the ring member 57 and an inner peripheral surface of the cover 15 (cover body 62), or between the bobbin structure 61 and the inner peripheral surface of the cover 15 (cover body 62). Thereby, when the cover 15 is rotated at a time of cover removal, the cover 15 does not come in contact with the elastic member 53 (ring member 57, bobbin structure 61).

Figure 10:
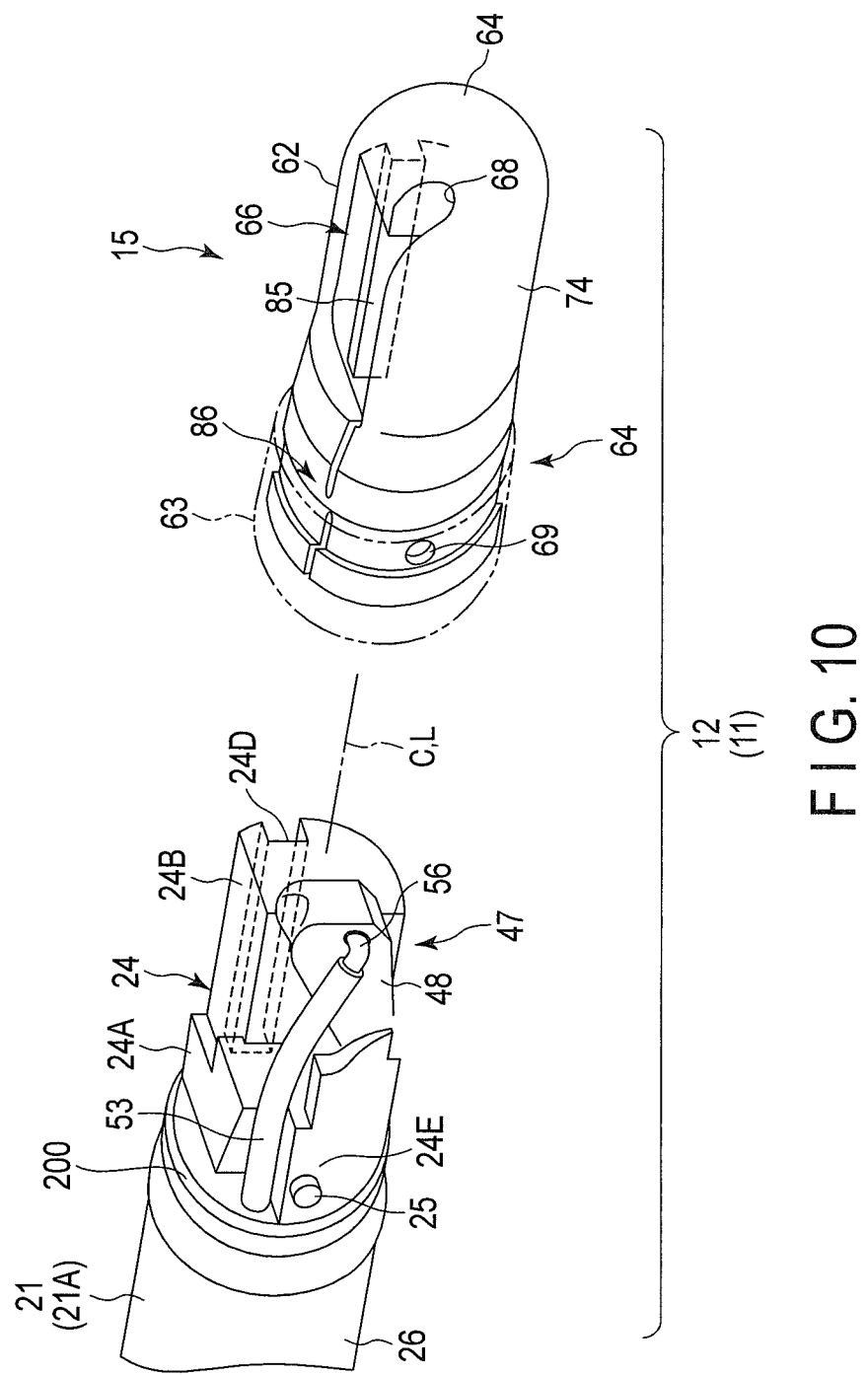
FIG. 10 is a perspective view illustrating a step of attaching the endoscope cover to the distal structure portion shown in FIG. 2.

As illustrated in FIG. 10, etc., the distal structure portion 24 includes a block-shaped main body 24A. As illustrated in FIG. 2, FIG. 3 and FIG. 5, in the main body 24A, a planar portion 24B (to be described later), a storage portion 24C (storage space), the wire moving section 52 (wire moving space), a guide groove 24D (first guide) and a pin fixing portion 24E are formed from a cylinder of rigid material such as stainless steel. In the main body 24A, a center axis C is defined. Incidentally, for the purpose of simple description, it is assumed that the above-described longitudinal axis L agrees with the center axis C.

As illustrated in FIG. 2, FIG. 3, FIG. 5 and FIG. 8, the main body 24A is provided with an illumination window 41 at the distal end of the illumination optical system 31; an observation window 42 at the distal end of the observation optical system 32; a distal portion of the tube 44 of the channel 36; and the pivot base 48 of the distal portion of the pivot mechanism 47. Thus, the distal structure portion 24 is formed of the main body 24A, the illumination window 41 of the illumination optical system 31, the observation window 42 of the observation optical system 32, the distal portion of the tube 44 of the channel 36, and also the pivot base 48 and wire 51 of the pivot mechanism 47.

The main body 24A includes the planar portion 24B in which the illumination window 41 and observation window 42 are fixed; the storage portion 24C which pivotably stores the pivot base 48; and the opening portion 46 which communicates with the storage portion 24C and with the channel 36, and guides the treatment instrument to the pivot base 48.

As illustrated in FIG. 8, the distal end of the tube 44 of the channel 36 is fixed in the opening portion 46. It is preferable that the distal side of the storage portion 24C along the longitudinal axis L, that is, the distal end of the main body 24A, is open. In the meantime, the wire moving section 52, which is continuous with the storage portion 24C and moves the wire 51, is formed on the proximal side of the storage portion 24C.

It is assumed that the planar portion 24B of the main body 24A is parallel to the longitudinal axis L. On the planar portion 24B of the main body 24, the illumination window 41 is arranged on the distal side, and the observation window 42 is arranged adjacent to the illumination widow 41 on the proximal side. In the meantime, the nozzle 34 is provided on the proximal side of the observation window 42. The nozzle 34 is directed toward the observation window 42 and illumination widow 41. The nozzle 34 can discharge a liquid, such as physiological saline, toward the observation window 42 and illumination widow 41, and can blow away, by air, a deposit on the observation window 42 and illumination widow 41.

The storage portion 24C is arranged in a direction perpendicular to the longitudinal axis L, relative to the planar portion 24B. The storage portion 24C forms a space in which the pivot base 48 can rotate within a predetermined range. The pivot base 48 is pivotably supported by the support pin 55, relative to the main body 24A.

In the pivot base 48, the distal end of the wire 51 of the pivot mechanism 47 is supported. In the meantime, the proximal end (not shown) of the wire 51 of the pivot mechanism 47 is supported by the lever 54 of the operation section 22. The length of the wire 51 is adjusted. Thus, when the lever 54 is set in a first position (the most pushed-up state shown in FIG. 1), the pivot base 48 is disposed in a position (fallen position) indicated by a solid line in FIG. 8. As the lever 54 is pushed down, the wire 51 is pulled and a distal end portion 48B of the pivot base 48, which is remote from the support pin 55, is raised, with the support pin 55 functioning as a fulcrum. In addition, the most pushed-down state of the lever is defined as a second position. At this time, the pivot base 48 is disposed at the most raised position, as indicated by a two-dot-and-dash line in FIG. 8.

As illustrated in FIG. 10, the main body 24A of the distal structure portion 24 includes, in its outer peripheral surface, the guide groove 24D (first restriction portion) as the first guide along the longitudinal axis L. The guide groove 24D neighbors the planar portion 24B, but is formed apart from the storage portion 24C, that is, the wire 51 and pivot base 48 of the pivot mechanism 47. It is preferable that the guide groove 24D is continuously formed from the distal end to proximal end of the main body 24A.

Figure 19:
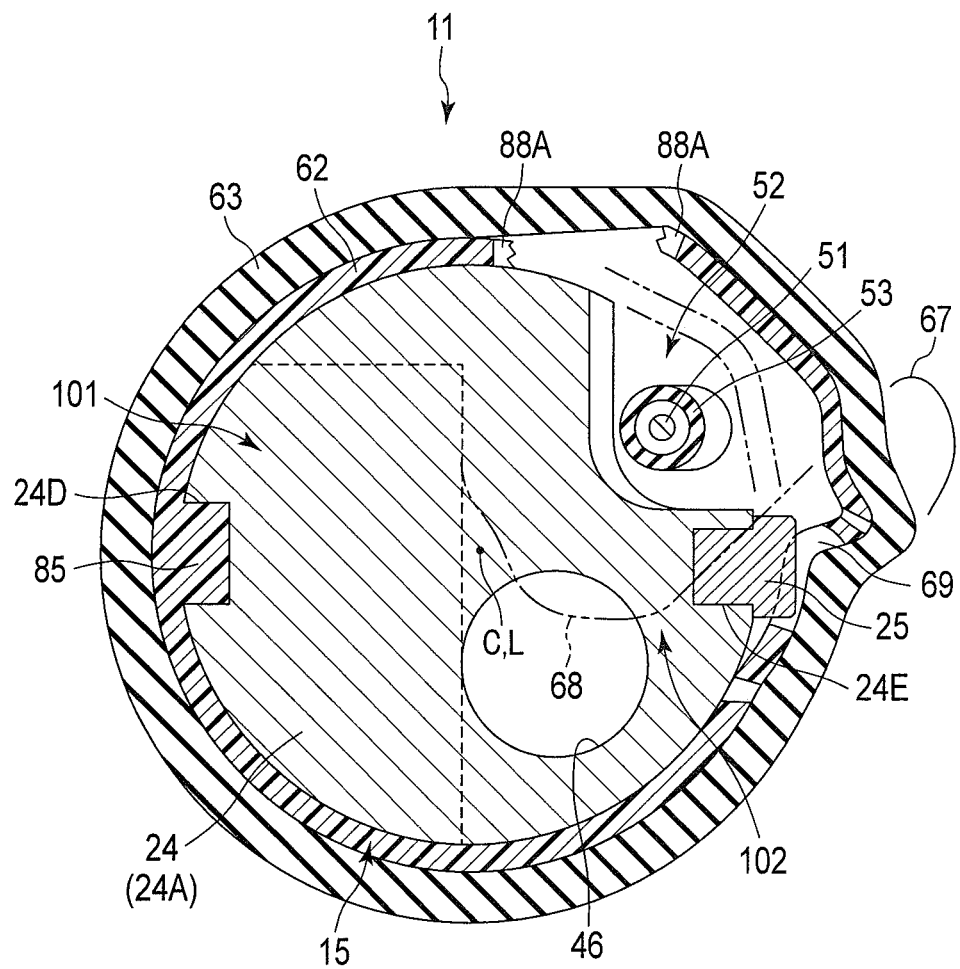
FIG. 19 is a cross-sectional view taken along line F19-F19 in FIG. 8, FIG. 19 illustrating the cover, distal structure portion and cover removing tool in a state after the cover removing tool was rotated by a predetermined angle relative to the cover, and broken portions were formed by breakage.

As illustrated in FIG. 10 and FIG. 19, in the main body 24A of the distal structure portion 24, the pin fixing portion 24E is formed on the outer peripheral surface thereof. It is preferable that the pin fixing portion 24E neighbors the wire moving section 52 and is formed substantially on the opposite side to the guide groove 24D, with the center axis C of the main body 24A of the distal structure portion 24 being interposed. The engaging pin 25 (engaging portion), which projects in a direction perpendicular to the center axis C, is fixed on the pin fixing portion 24E. The engaging pin 25 is formed in a columnar shape, but the shape of the engaging pin 25 is not limited to the columnar shape. An inclined surface may be provided on the engaging pin 25 on the side of the wire moving section 52 (or the distal side), so that the engaging pin 25 may easily be disengaged from an engaging recess portion 69.

Figure 4:
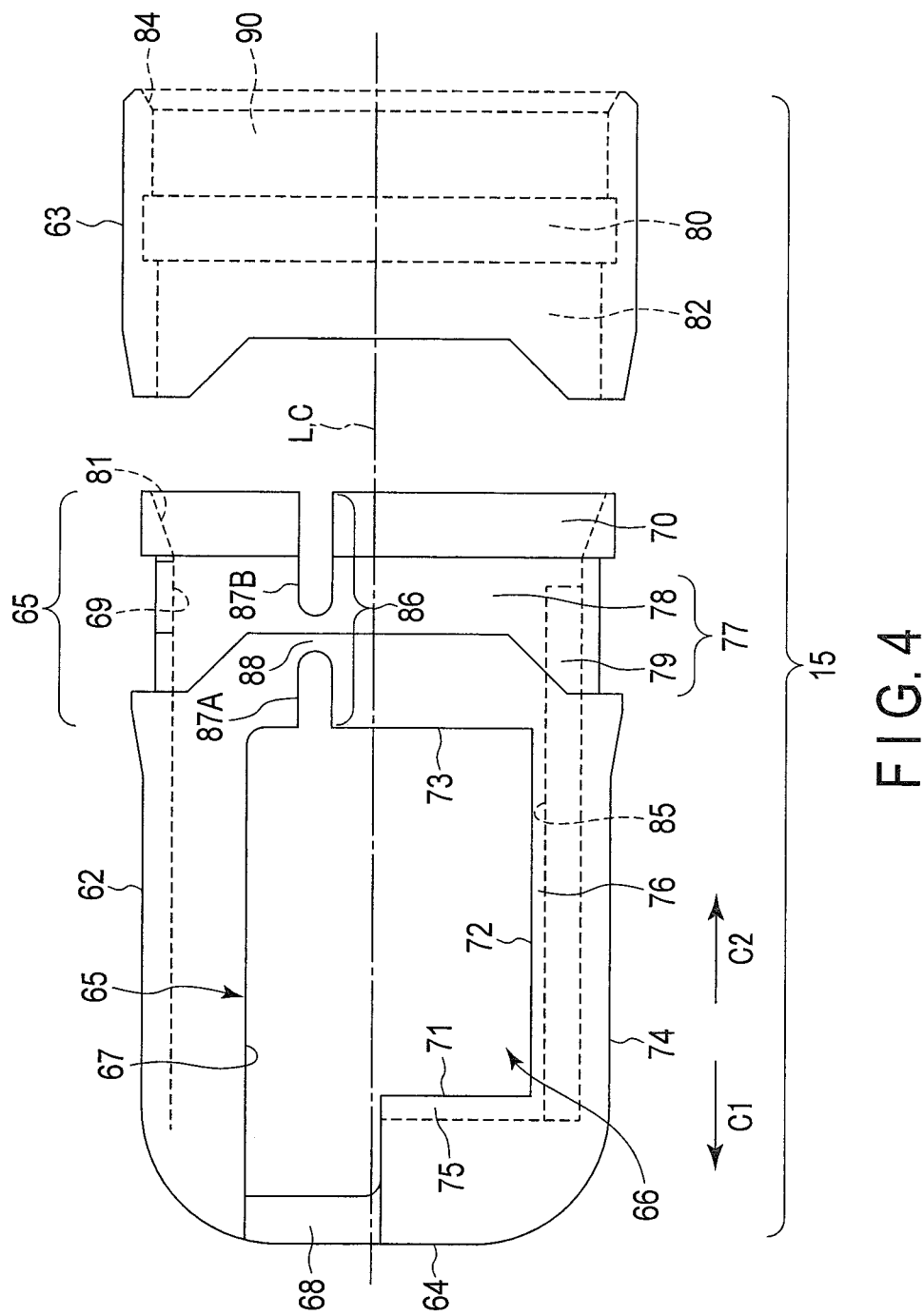
FIG. 4 is a plan view illustrating a cover body and a ferrule of the cover illustrated in FIG. 3.

As illustrated in FIG. 3 and FIG. 4, the cover 15 includes a cover body 62 and a ferrule 63. The cover body 62 is formed of, for example, a resin material, in an integral cylindrical shape. The ferrule 63 is formed of, for example, a rubber material, in a cylindrical or annular shape. Incidentally, it is preferable that the cover body 62 and ferrule 63 are formed of a material with electrical insulating properties. In addition, the inside diameters, or the inner peripheral surfaces, of the cover body 62 and ferrule 63 are formed to have proper sizes and shapes, based on the size of the distal structure portion 24.

The cover body 62 includes a closing portion 64 at its distal end, and includes an annular portion 65 at its proximal end. The closing portion 64 is formed in a substantially hemispheric shape. The proximal end of the cover body 62, that is, the annular portion 65, is opened. The cover body 62 includes a substantially rectangular opening edge portion 66 (opening portion) between the closing portion 64 and annular portion 65. The opening edge portion 66 exposes the illumination window 41, observation window 42, nozzle 34 and pivot base 48 of the distal structure portion 24 to the outside.

As illustrated in FIG. 3 and FIG. 4, the opening edge portion 66 (opening portion) includes a right-side edge portion 67 which is provided on the right side along the longitudinal axis L from the proximal direction C2 side toward the distal direction C1 side; a U-shaped recess portion 68 which is continuous with the right-side edge portion 67; a distal edge portion 71 which is continuous with the recess portion 68; a left-side edge portion 72 which is continuous with the recess portion 68 and is provided on the left side along the longitudinal axis L from the proximal direction C2 side toward the distal direction C1 side; and a proximal edge portion 73 which is provided between the right-side edge portion 67 and left-side edge portion 72. The opening edge portion 66 forms a closed loop by the right-side edge portion 67, recess portion 68, distal edge portion 71, left-side edge portion 72 and proximal edge portion 73. It is preferable that the right-side edge portion 67 and left-side edge portion 72 are parallel or substantially parallel to each other. It is preferable that the distal edge portion 71 and proximal edge portion 73 are parallel or substantially parallel to each other. When the pivot base 48 pivotally moves the treatment instrument, the endoscope 12 exposes the pivot base 48 from the opening edge portion 66 (opening portion) (see FIG. 8).

The right-side edge portion 67, together with the annular portion 65 and a rotational circumferential surface 74 (to be described later), covers the wire 51 and elastic member 53 of the pivot mechanism 47 such that the wire 51 and elastic member 53 are movable. The distal edge portion 71 includes a distal covering portion 75 which covers the distal direction C1 side of the planar portion 24B of the main body 24A, with respect to the illumination window 41. Similarly, the left-side edge portion 72 includes a left-side covering portion 76 which covers the left side of the planar portion 24B of the main body 24A, with respect to the illumination window 41 and observation window 42.

Figure 9:
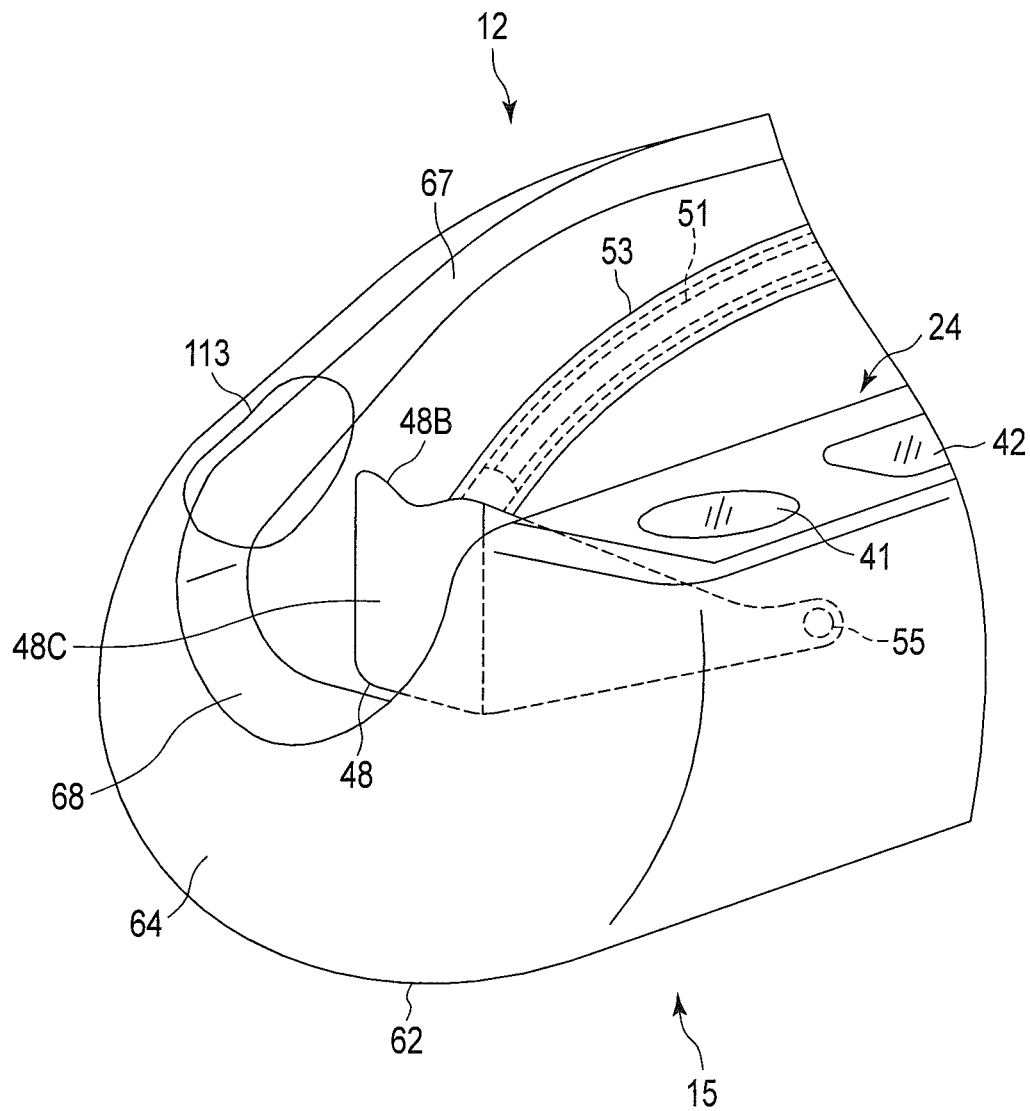
FIG. 9 is a perspective view illustrating, in enlarged scale, the distal structure portion and cover shown in FIG. 3.

As illustrated in FIG. 4 and FIG. 9, the U-shaped recess portion 68, which is continuous with the right-side edge portion 67, is formed at a distal end of the right-side edge portion 67. The recess portion 68 is formed toward the closing portion 64. A part, in which the recess portion 68 is formed, is tapered toward the distal direction C1 side along the longitudinal axis L (see FIG. 8).

As illustrated in FIG. 4, the annular portion 65 includes, on its outer peripheral surface, an engaging portion 77 with which the ferrule 63 is engaged. The engaging portion 77 is formed at a position spaced apart toward the proximal direction C2 side along the longitudinal axis L from the proximal edge portion 73 of the opening edge portion 66. The engaging portion 77 includes an annular recess portion 78 which suppresses a movement of the ferrule 63 along the longitudinal axis L relative to the cover body 62; and an engaging recess portion 79 which suppresses a movement of the ferrule 63 around the longitudinal axis L. The annular recess portion 78 and engaging recess portion 79 are integrally continuously formed. In the annular portion 65, an annular flange portion 70 is formed at a distal end of the engaging portion 77, the annular flange portion 70 projecting radially outward with respect to the longitudinal axis L, relative to the annular recess portion 78. A skirt portion 81, which has a gradually decreasing thickness toward the proximal side along the longitudinal axis L, is formed on the inner periphery of the flange portion 70. The skirt portion 81 has a gradually increasing inside diameter toward the proximal side. It is preferable that the skirt portion 81 has a taper shape.

In the meantime, it is preferable that the inside diameter of the inner peripheral surface of the cover body 62 is constant from the vicinity of the distal end of the right-side edge portion 67 of the opening edge portion 66, and from the vicinity of the distal end of the left-side edge portion 72, to the distal end of the skirt portion 81 of the flange portion 70.

The ferrule 63 includes, on its inner peripheral surface, an annular projection portion 82 which is engaged in the annular recess portion 78. The ferrule 63 includes, on its inner peripheral surface, an annular engaging recess portion 80 in which the flange portion 70 is engaged. Thus, as illustrated in FIG. 3, the ferrule 63 is engaged with the annular portion 65 of the cover body 62. As illustrated in FIG. 4 and FIG. 5, the ferrule 63 includes, on its inner peripheral surface, a second skirt portion 84 in which a bobbin portion 83 of the distal portion of the bending portion 26 is engaged. The second skirt portion 84 has a gradually decreasing thickness toward the proximal side along the longitudinal axis L, and has a gradually increasing inside diameter toward the proximal direction C2 side. It is preferable that the second skirt portion 84 has a taper shape.

As illustrated in FIG. 4 and FIG. 10, an engaging recess portion 69 (engaging portion), which is engageable with the engaging pin 25, is formed in an inner peripheral surface of the annular portion 65 of the proximal end of the cover body 62. The engaging recess portion 69 may be formed in such a state that the inner peripheral surface and outer peripheral surface of the cover body 62 communicate with each other, or may be simply formed in a recess shape in the inner peripheral surface of the cover body 62. It is preferable that the engaging recess portion 69 is formed in the annular recess portion 78.

A guide projection portion 85, which is movable along the guide groove 24D, is formed on the inner peripheral surface of the cover body 62. Specifically, the guide projection portion 85 projects radially inward from the inner peripheral surface of the cover body 62. It is preferable that the guide projection portion 85 is formed from the vicinity of the distal end of the inner peripheral surface of the cover body 62 to the vicinity of the proximal end thereof. The guide projection portion 85 can be formed in a proper shape. For example, as illustrated in FIG. 10, the guide projection portion 85 has a transverse cross section which is formed in a substantially rectangular shape in a manner to correspond to the shape of the guide groove 24D. Besides, although not illustrated, the guide projection portion 85 may be composed of a plurality of guide projection portions, and these guide projection portions may be mutually spaced apart at proper intervals.

As illustrated in FIG. 4, a fragile portion 86 is formed between the proximal edge portion 73 of the opening edge portion 66 of the cover body 62 and the proximal end of the flange portion 70 of the annular portion 65. The fragile portion 86 is decreased in strength and made fragile, compared to the other parts, and the fragile 86 is destroyed when the cover 15 is removed from the distal structure portion 24. Here, the fragile portion 86 includes slits 87A and 87B, and a coupling portion 88 (broken portions 88A) which is located between the slits 87A and 87B. One slit 87A is formed continuous with the proximal edge portion 73 of the opening edge portion 66. The other slit 87B is formed continuous with the proximal end of the flange portion 70 of the annular portion 65. In this case, the slits 87A and 87B are formed along the longitudinal axis L. The slits 87A and 87B do not communicate with each other, and the coupling portion 88 is formed. In the meantime, the engaging recess portion 69 is formed at a position rotated by about 90° from the coupling portion 88 around the center axis C. In addition, the guide projection portion 85 is formed at a position rotated by about 90° from the coupling portion 88 around the center axis C in a circumferential direction on the side opposite to the engaging recess portion 69. Incidentally, as will be described later, it is more preferable that the fragile portion 86 is spaced apart from the guide projection portion 85 over 90° or more, and the distance between the fragile portion 86 and engaging recess portion 69 is smaller than the distance between the guide projection portion 85 and fragile portion 86.

As illustrated in FIG. 3, it is preferable that the fragile portion 86 is disposed not on the planar portion 24B of the main body 24A of the distal structure portion 24, but on the wire moving section 52 (wire moving space). The slits 87A and 87B on the proximal direction C2 side contribute to elastic deformation of the annular portion 65. Specifically, when the engaging recess portion 69 is engaged with the engaging pin 25, the flange portion 70 of the annular portion 65 is elastically deformable. Incidentally, the position of the coupling portion 88 of the fragile portion 86 is not limited to the position shown in FIG. 3. The coupling portion 88 may be provided on a position on the flange portion 70 on the proximal direction C2 side of the annular portion 65, or may be provided on a position facing the opening edge portion 66 on the distal direction C1 side of the annular portion 65.

As illustrated in FIG. 2, the cover body 62 includes the rotational circumferential surface 74 on its outer periphery. The rotational circumferential surface 74 is formed as a part of the cylinder. The center axis C of the cover 15 and distal structure portion 24 is defined by the rotational circumferential surface 74. This rotational circumferential surface 74 is engaged with a support circumferential surface 91 (to be described later) of the cover removing tool 16.

When the cover 15 is formed, the ferrule 63 is attached to the cover body 62 shown in FIG. 4. At this time, to begin with, it is confirmed that the coupling portion 88 exists between the slits 87A and 87B of the cover body 62, and the slits 87A and 87B do not communicate with each other. Thereafter, the ferrule 63 is engaged with the cover body 62, thereby forming the cover 15.

As illustrated in FIG. 10, the cover 15 is attached to the distal structure portion 24 by defining the direction of the cover 15 in the circumferential direction about the longitudinal axis L. At this time, the guide projection portion 85 of the cover 15 is engaged in the guide groove 24D of the main body 24A of the distal structure portion 24, and the guide projection portion 85 is moved along the longitudinal axis L. Thus, misalignment in the circumferential direction of the cover 15 in relation to the distal structure portion 24 is prevented.

In addition, when the cover 15 is attached to the distal structure portion 24, the skirt portion 81 of the engaging portion 90 of the ferrule 63 of the cover 15 is abutted on the engaging pin 25 of the distal structure portion 24. At this time, the engaging portion 90 elastically deforms by its elasticity, and passes over the engaging pin 25. Thus, the skirt portion 81 of the annular portion 65 of the cover body 62 abuts on the engaging pin 25 of the distal structure portion 24. At this time, the annular portion 65 elastically deforms by the slits 87A and 87B, and passes over the engaging pin 25. Thus, the engaging recess portion 69 is engaged with the engaging pin 25 of the distal structure portion 24.

In addition, the skirt portion 81 of the engaging portion 90 of the ferrule 63 abuts on the bobbin portion 83 at the distal end of the bending portion 26 and an insulating member 200 on the front side of the bobbin portion 83. Incidentally, the bobbin portion 83 is a part where an adhesive was applied from the outer periphery of the string which is annually wound, and the applied adhesive was fixed.

At this time, as illustrated in FIG. 2 and FIG. 3, the illumination window 41, observation window 42 and nozzle 34 are exposed to the opening edge portion 66 of the cover 15, and the pivot base 48 is exposed such that the pivot base 48 is pivotable within a proper range. As illustrated in FIG. 9, in the state in which the cover 15 is properly attached to the distal structure portion 24, a part of a distal surface 48C and the distal end portion 48B of the pivot base 48 are exposed, as viewed from the distal side along the longitudinal axis L. Thus, when the treatment instrument (not shown) is guided by the pivot base 48 and projected from the distal end of the pivot base 48, the recess portion 68 prevents the treatment instrument from interfering with the cover 15.

In the meantime, in the state in which the cover 15 is attached to the distal structure portion 24, when the cover 15 is viewed in a cross section perpendicular to the longitudinal axis L, as illustrated in FIG. 19, the cross section is divided into a first region 101 and a second region 102. In this case, the guide projection portion 85 is located in the first region 101, and the engaging recess portion 69 is located in the second region 102.

In the endoscope 12, the insertion section 21 is inserted into a tract such as a lumen cavity, in the state in which the cover 15 is attached to the distal structure portion 24. Thus, observation and a proper treatment are performed. Incidentally, the fragile portion 86 is covered and protected by the ferrule 63. Thus, for example, during the insertion into a tract such as a lumen cavity, or during a treatment, even if the fragile portion 86 abuts on an inner wall or the like, breakage of the fragile portion 86 is prevented.

After the use of the endoscope 12, the cover 15 and ferrule 63 are removed from the distal structure portion 24, and are discarded. Specifically, in the state in which the cover 15 is removed, the endoscope 12 (the distal structure portion 24 of the endoscope 12) is cleaned, disinfected and sterilized, and is reused. At this time, since the cover 15 is removed from the distal structure portion 24, the channel 36 and pivot mechanism 47, as well as the vicinity of the illumination window 41 of the illumination optical system 31 and the vicinity of the observation window 42 of the observation optical system 32, are easily cleaned.

In the meantime, when the cover 15 is removed from the distal structure portion 24, it is not impossible to remove the cover 15 by ripping the coupling portion 88 between the slits 87A and 87B by using the force of the user's fingers. However, when the cover 15 is removed from the distal structure portion 24 by the user's fingers, the manner of removal may differ from user to user. Thus, there is concern that it is difficult to stably destroy the fragile portion 86.

The fragile portion 86 can stably be destroyed by using the cover removing tool 16 (see FIG. 11 to FIG. 15). It is thus preferable to use the cover removing tool 16 at a time of removing the cover 15 from the distal end portion 24 after the use of the endoscope 12.

The cover removing tool 16 according to the present embodiment is formed of a resin material having higher rigidity than the cover body 62 of the cover 15. Specifically, while the cover 15 is formed of a general resin material such as a plastic, a fiber reinforced plastic such as a glass fiber reinforced plastic can be used for the cover removing tool 16. On the other hand, the distal structure portion 24 is formed of a general metallic material (stainless steel, etc.). Specifically, the cover removing tool 16 is formed of a material which is harder than the cover 15 (cover body 62) and is softer than the distal structure portion 24. Thereby, the fragile portion 86 of the cover 15 can easily be destroyed, and the distal structure portion 24 is prevented from being accidentally damaged.

As illustrated in FIG. 11, the cover removing tool 16 includes a columnar body 103. The outer periphery of the columnar body 103 is formed in a proper shape. As illustrated in FIG. 11, a working portion 104, which acts at a time of removing the cover 15 that is attached to the distal structure portion 24, is formed at one end 103A of the columnar body 103. The working portion 104 is formed in such a recess shape as to cover the vicinity of the closing portion 64 of the cover 15. An index 105, which enables the user to recognize the direction of the cover removing tool 16 in the circumferential direction around the longitudinal axis L, is formed on an outer peripheral surface of the columnar body 103. Here, the index 105 is formed as such a planar surface as to enable recognition of the direction by the touch. It is preferable that the index 105 is formed at a position neighboring the working portion 104.

The index 105 enables the user to recognize, by the naked eyes, etc., the position of insertion relative to the distal structure portion 24 to which the cover 15 is attached. The index 105 may be characters such as "UP", or may be an imprinted arrow indicative of the rotational direction. In this manner, the outer shape of the cover removing tool 16 is not particularly limited.

As illustrated in FIG. 12 and FIG. 13, the working portion 104 includes a bottom surface 106; a support circumferential surface 91 which is, preferably, perpendicular to the bottom surface 106; a first projection portion 107 (projection) is engaged in the U-shaped recess portion 68 of the opening edge portion 66 of the cover 15; a second projection 108 which is engaged with the distal covering portion 75 of the cover body 62, which is flush with the planar portion 24B; a run-off portion 109 in which a part of the right-side edge portion 67 of the opening edge portion 66 of the destroyed cover 15 is disposed. The first projection portion 107 (projection) includes a stepped portion 110 extending in the longitudinal axis L direction; an inclined portion 111 which is inclined in a direction away from the center axis C toward the proximal direction C2 side of the center axis C direction; and a top surface portion 112 provided on the proximal direction C2 side of the center axis C direction. As illustrated in FIG. 8, the inclined portion 111 extends in a direction along a locus A which the distal end portion 48B of the pivot base 48 describes, at a position apart from the locus A. Thus, even if the pivot base 48 rotates by a small distance in the state in which the cover removing tool 16 is engaged with the cover 15, the distal end portion 48B of the pivot base 48 does not interfere with the inclined portion 111.

As illustrated in FIG. 8, in the state in which the cover removing tool 16 is engaged with the cover, a predetermined gap G2 is provided along the longitudinal axis L direction between the top surface portion 112 and the one end 53B of the elastic member 53. This gap G2 is formed in the state (the state indicated by a solid line in FIG. 8) in which the pivot base 48 is located most on the distal direction C1 side in the longitudinal axis L direction. Thus, when the cover removing tool 16 is rotated, the first projection portion 107 does not damage the elastic member 53 by coming in contact with the elastic member 53.

Figure 14:
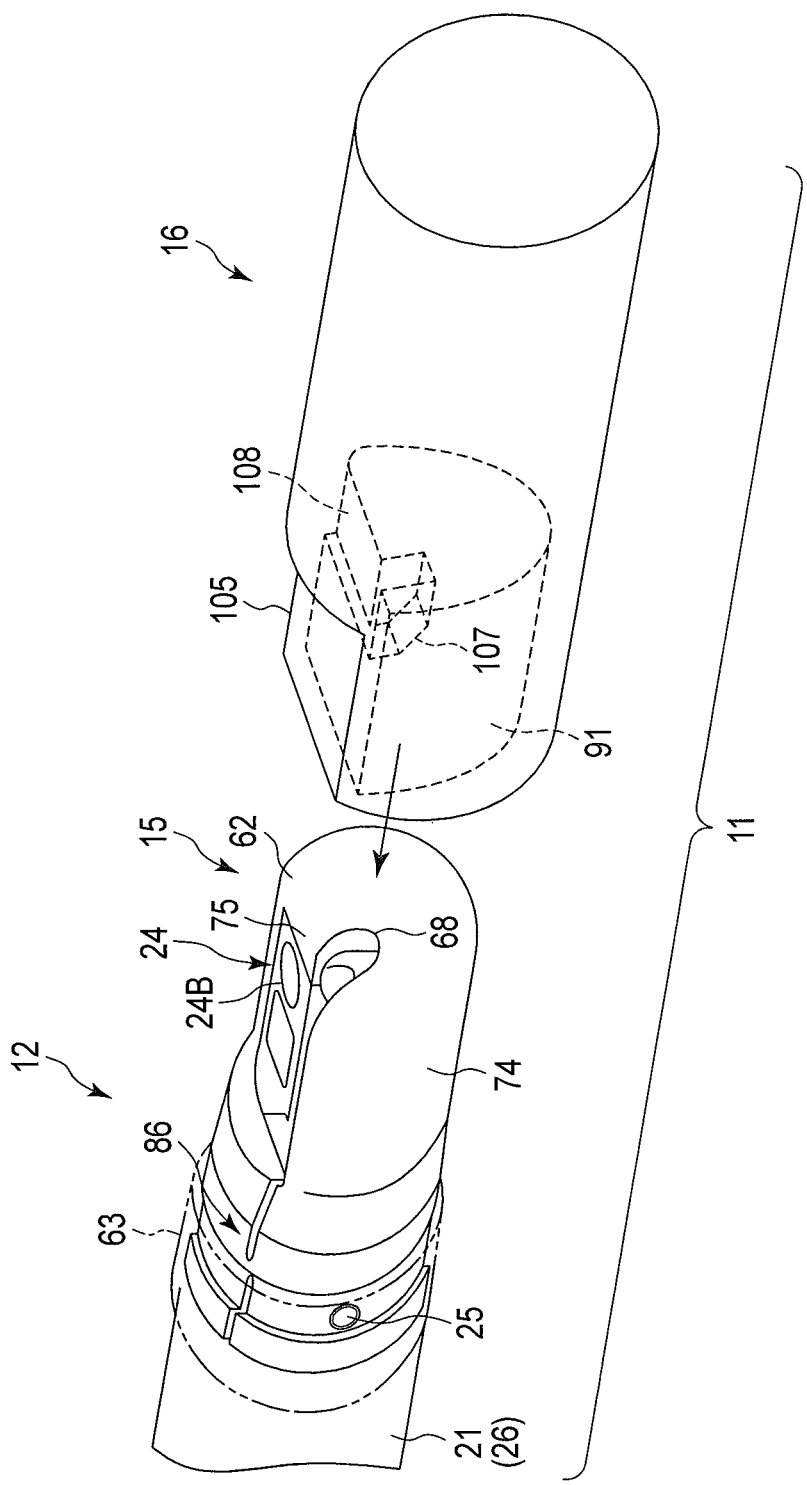
FIG. 14 is a perspective view illustrating, at an angle different from the angle in FIG. 11, the step of attaching the cover removing tool of the endoscope system to the cover of the endoscope.

As illustrated in FIG. 14 and FIG. 15, the working portion 104 at one end 103A of the columnar body 103 of the cover removing tool 16 is engaged with the distal structure portion 24 to which the cover 15 is attached. As illustrated in FIG. 8, a distal surface of the closing portion 64 of the cover 15 abuts on the bottom surface 106. Thus, the bottom surface 106 defines a fixed length of that part of the cover 15, which is inserted into the recess-shaped working portion 104, with respect to the one end 103A of the cover removing tool 16.

As illustrated in FIG. 12, the support circumferential surface 91 is formed as a part of the cylinder. By the support circumferential surface 91, the center axis C of the working portion 104 is defined. The distance, i.e. the radius, between the center axis C and the support circumferential surface 91, is set to be slightly greater than the radius defined by the rotational circumferential surface 74 of the cover 15. Thus, the rotational circumferential surface 74 of the cover 15 is abutted on, and supported by, the support circumferential surface 91. At this time, the support circumferential surface 91 is movable relative to the rotational circumferential surface 74 around the center axis C (see FIG. 16 and FIG. 17).

The width of the first projection portion 107 is set to be slightly smaller than the width of the recess portion 68 of the cover 15. As illustrated in FIG. 13, the first projection portion 107 of the cover removing tool 16 includes a pushing portion 114. The pushing portion 114 is abutted on a to-be-pushed portion (edge) 113 (see FIG. 9) between the recess portion 68 and right-side edge portion 67 of the opening edge portion 66 of the cover 15.

The second projection portion 108 shown in FIG. 12 projects toward the one end 103A of the columnar body 103, relative to the bottom surface 106. The second projection portion 108 neighbors the first projection portion 107 in the circumferential direction about the center axis C. It is preferable that the second projection portion 108 is parallel to the planar portion 24B. The second projection portion 108 can be abutted on the distal covering portion 75 of the distal edge portion 71 of the cover 15 (see FIG. 14).

The function of the cover removing tool 16 for removing the cover 15, which is attached to the distal structure portion 24, will be described.

As illustrated in FIG. 11 and FIG. 14, the working portion 104 of the cover removing tool 16 is opposed to the distal structure portion 24 to which the cover 15 is attached. The direction of the index 105 is set in a parallel state to the planar portion 24B of the distal structure portion 24. As illustrated in FIG. 8 and FIG. 15, in this state, the working portion 104 of the cover removing tool 16 is engaged with the distal structure portion 24 to which the cover 15 is attached. The center axis C of the support circumferential surface 91 of the cover removing tool 16 is aligned with the center axis C of the rotational circumferential surface 74 of the cover 15, and the distal surface of the closing portion 64 of the cover 15 is abutted on the bottom surface 106 of the working portion 104 of the cover removing portion 16.

As illustrated in FIG. 16, at this time, the first projection portion 107 of the cover removing tool 16 is engaged in the recess portion 68 of the opening edge portion 66 of the cover 15. The second projection portion 108 of the cover removing tool 16 is disposed close to, or abutted on, the distal covering portion 75 of the cover 15.

In the state in which the distal structure portion 24 or the vicinity of the distal portion of the insertion section 21 is held and the distal surface of the closing portion 64 of the cover 15 is abutted on the bottom surface 106 of the cover removing tool 16, the cover removing tool 16 is rotated in a direction indicated by an arrow R in FIG. 15, relative to the distal structure portion 24 and the cover 15. Specifically, relative to the rotational circumferential surface 74 of the cover 15, the support circumferential surface 91 of the cover removing tool 16, which has the common center axis C to the rotational circumferential surface 74, is rotated about the center axis C.

Thereby, as illustrated in FIG. 16 and FIG. 17, while the opposed surface of the second projection portion 108 is moved away from the distal covering portion 75, the pushing portion 114 of the first projection portion 107 pushes the to-be-pushed portion (edge) 113 of the right-side edge portion 67 of the opening edge portion 66.

At this time, the guide projection portion 85 of the cover 15 tries to keep the state in which the guide projection portion 85 is engaged in the guide groove 24D of the distal structure portion 24. Thus, the guide projection portion 85 restricts the movement of the cover body 62 about the center axis C, relative to the distal structure portion 24.

Accordingly, the amount of working force of the cover removing tool 16 is applied to the coupling portion 88 between the slits 87A and 87B of the cover 15, which is opposed to the first projection portion 107 of the cover removing tool 16, through the to-be-pushed portion 113, right-side edge portion 67 and proximal edge portion 73. Thereby, a stress concentrates at the fragile portion 86 of the cover 15, and the coupling portion 88 is broken as illustrated in FIG. 19. By the breakage of the coupling portion 88, that part of the engaging portion 77 of the annular portion 65, which includes the engaging recess portion 69, moves in the circumferential direction, while the state is maintained in which the guide projection portion 85 of the cover 15 is engaged in the guide groove 24D of the distal structure portion 24. At this time, by the momentum of release of the stress due to the breakage of the coupling portion 88 of the fragile portion 86, the engaging recess portion 69 of the cover 15 can be disengaged from the engaging pin 25 of the distal structure portion 24. Thus, the breakage of the fragile portion 86 and the disengagement between the engaging pin 25 and the engaging recess portion 69 can be performed substantially at the same time.

In the present embodiment, in particular, the distance of engagement between the guide groove 24D of the distal structure portion 24 and the guide projection portion 85 of the cover 15 is set to be long. Thus, when the cover 15 is destroyed by using the cover removing tool 16, the pushing force on the cover 15 is more concentrated for the breakage of the fragile portion 86 and the disengagement between the engaging pin 25 and the engaging recess portion 69.

In the meantime, as illustrated in FIG. 17, the right-side edge portion 67 enters the run-off portion 109 of the cover removing tool 16. If the cover removing tool 16 is further rotated in the direction of arrow R in FIG. 15, relative to the distal structure portion 24 or the cover 15, the user of the cover removing tool 16 is required to apply a force for bending the right-side edge portion 67. Thus, the support circumferential surface 91 of the cover removing tool 16 becomes less easily slidable around the center axis C, relative to the rotational circumferential surface 74 of the cover 15. The user of the cover removing tool 16 recognizes this state. Accordingly, if the user of the cover removing tool 16 rotates the cover removing tool 16 in the direction of arrow R in FIG. 15, relative to the distal structure portion 24 or the cover 15, the user feels a proper drag until the coupling portion 88 is broken and the engagement between the engaging pin 25 and engaging recess portion 69 is released. Thereafter, the drag decreases, and then increases once again. By feeling the second drag, the user can recognize that the breakage of the coupling portion 88 is completed.

At this time, the first projection portion 107 and second projection portion 108 come in contact with none of parts of the distal structure portion 24. Thus, when the cover 15 is removed from the distal structure portion 24 by the cover removing tool 16, a load is prevented from acting on the distal structure portion 24. In short, the distal structure portion 24 is not damaged.

In addition, the cover removing tool 16 is drawn out to the distal direction C1 side along the longitudinal axis L, from the cover 15 in which the fragile portion 86 was broken and broken portions 88A were formed. Thus, as illustrated in FIG. 18, the user can directly observe the state in which the fragile portion 86 was broken. Since the fragile portion 86 was broken and the engaging recess portion 69 was disengaged from the engaging pin 25 of the distal structure portion 24, the cover 15 can be held by the user's fingers, a forceps, etc., and removed from the distal structure portion 24 to the distal direction C1 side along the longitudinal axis L. Thus, if the cover removing tool 16 is used, the user can more easily remove the cover 15 in the state in which the hygienic safety for the user (surgeon or staff) is secured. Incidentally, depending on the state of breakage, there may be a case in which the cover 15, together with the cover removing tool 16, is removed from the distal structure portion 24.

The removed cover 15 is discarded. The endoscope 12, from which the cover 15 was removed, that is, the insertion section 21 including the distal structure portion 24, the operation section 22 and the universal cord 23, are properly cleaned, disinfected and sterilized for reuse. In addition, a new cover 15 is properly attached to the distal structure portion 24, and observation and a treatment are performed.

In the meantime, the cover removing tool 16, as well as the cover 15, may be thrown away after use. In this case, it is preferable that a set of the cover 15 and cover removing tool 16 is sold as a cover unit. In addition, it is preferable that a set of the endoscope 12 and cover removing tool 16 is sold as the endoscope system 11.

In the state in which the distal structure portion 24 is held, if the cover removing tool 16 is rotated in a direction opposite to the direction indicated by the arrow R in FIG. 15, relative to the distal structure portion 24 and cover 15, the first projection portion 107 of the cover removing tool 16 pushes the wall surface of the storage portion 24C. In addition, the state is maintained in which the opposed surface of the second projection portion 108 abuts on the distal covering portion 75 of the distal edge portion 71 of the cover 15. Thus, it is not possible that the user erroneously rotates the cover removing tool 16 in the direction opposite to the direction indicated by the arrow R in FIG. 15.

As has been described above, according to the endoscope 12 of this embodiment, the following can be said. The endoscope system 11 includes the insertion section 21 which is inserted into a lumen cavity along the longitudinal axis L; the distal structure portion 24 provided at the distal end of the insertion section 21; the pivot base 48 configured to pivotally move the treatment instrument at the distal end of the insertion section 21; the elongated pulling member connected to the pivot base 48 in the distal structure portion 24, and configured to remotely operate the pivot base 48; the tubular elastic member 53 configured to cover the pulling member, the elastic member 53 including one end water-tightly connected to the distal side of the pulling member or the pivot base 48, and the other end water-tightly connected to the distal structure portion 24; the cylindrical cover 15 configured to be attached to the distal structure portion 24, and including the opening portion in the peripheral surface thereof; the cover removing tool 16 configured to be capable of pushing the edge of the opening portion, in the state in which the cover removing tool 16 is engaged with the cover 15; and the projection provided on the cover removing tool 16, the projection being configured to come in contact with the edge of the opening portion at a position apart from a position of the one end 53B of the elastic member 53 in the direction of the longitudinal axis L, in the state in which the cover removing tool 16 is engaged with the cover 15.

According to this configuration, the cover 15 can be removed by the cover removing tool 16 at a position apart from the elastic member 53. Thus, when the removing work is performed, the work can be safely performed without damaging the elastic member 53. The cover 15, which is of a disposable type, can be used for the distal structure portion 24. Thus, for example, even the back side of the pivot base 48, or the like, is easily and surely cleaned by using, for example, a brush or the like.

In addition, in usual cases, the cover 15 is very small, compared to the size of the user's hand. Thus, there is difficulty in removing the cover 15. On the other hand, when the cover removing tool 16 is used, the cover 15 can always easily be removed from the distal structure portion 24 by a fixed operation. Furthermore, when the cover removing tool 16 is used, at least a part of the fragile portion 86 is exposed. Thus, the work of destroying the fragile portion 86 can be performed while the fragile portion 86 is directly being observed by the naked eyes.

Besides, when the cover 15 is removed from the distal structure portion 24 by using the cover removing tool 16, none of the locations of the cover removing tool 16 come in contact with the distal structure portion 24 from the beginning to end of the application of stress by the removal. Thus, a load is prevented from acting on the distal structure portion 24 by the cover removing tool 16.

In the state in which the pivot base 48 is located most on the distal direction C1 side in the longitudinal axis L direction, the above-described projection is provided at the position apart from the one end 53B of the elastic member 53 in the longitudinal axis L direction. According to this configuration, even when the elastic member 53 is located most on the distal direction C1 side in the longitudinal axis L direction, the projection can be disposed at the position apart from the elastic member 53. Thus, the work of removing the cover 15 can be safely performed without damaging the elastic member 53.

When the pivot base 48 pivotally moves the treatment instrument, the pivot base 48 is exposed from the opening portion. According to this configuration, the cover 15 can be removed by pushing the opening portion (opening edge portion 66) for exposing the pivot base 48. Thus, there is no need to provide the cover 15 with a hook portion for removal, and the structure of the cover 15 can be simplified.

The cover 15 includes the annular portion 65, and the fragile portion 86 provided on the annular portion 65 such that at least a part of the fragile portion 86 faces the opening portion, the fragile portion 86 having a lower strength than the other part of the annular portion 65. According to this configuration, by the fragile portion 86, the annular portion 65 can easily be broken with a small force, the efficiency of work at a time of removing the cover 15 can be improved, and the load on the user can be reduced.

The projection pushes the edge of the opening portion when the cover removing tool 16 is rotated about the center axis C thereof. Accordingly to this configuration, the cover 15 can be removed by rotating the cover removing tool 16 about the center axis C, and it is possible to further reduce the risk of an interference between the projection and the elastic member 53 at the time of the work for removal.

In the present embodiment, the example was described in which the engaging pin 25, which projects radially outward, is disposed on the distal structure portion 24, and the engaging recess portion 69 is formed in the endoscope cover 15. However, the relationship of the projection and recess may be reversed. Specifically, it is also preferable that the engaging recess portion 69 is formed in the distal structure portion 24, and the engaging pin 25, which is engageable in the engaging recess portion 69, is formed on the endoscope cover 15.

First Modification

Referring to FIG. 20, a first modification of the endoscope system 11 described in the embodiment will be described. Here, the positional relationship between the fragile portion 86 of the cover 15 and the other end 53C of the elastic member 53 is different. As illustrated in FIG. 20, the coupling portion 88 (broken portions 88A) of the fragile portion 86 is located on the proximal direction C2 side with respect to the other end 53C of the elastic member 53 in the longitudinal axis L direction.

Specifically, in the present modification, the position of the other end 53C of the elastic member 53, which is located on the opposite side to the one end 53B of the elastic member 53, is provided at a position apart from the broken portions 88A, which are portions to be broken in the fragile portion 86, in the longitudinal axis L direction. Thus, when the cover removing tool 16 is rotated, even if the broken portions 88A of the coupling portion 88 move inward (toward the distal structure portion 24), the broken portions 88A of the coupling portion 88 are prevented from damaging the elastic member 53.

Second Modification

Referring to FIG. 21, a second modification of the endoscope system 11 described in the embodiment will be described. Here, the shape of the distal structure portion 24 is different.

As illustrated in FIG. 21, the distal structure portion 24 includes a partition wall 115. The partition wall 115 provides a partition between the wire moving section 52, in which the wire 15 (pulling member) and elastic member 53 are located, and the cover body 62. The partition wall 115 is provided integral with the main body 24A of the distal structure portion 24.

In the present modification, the elastic member 53 is covered by the partition wall 115. Thus, even if the broken portions 88A of the coupling portion 88 move inward (toward the distal structure portion 24) after the fragile portion 86 is broken, the partition wall 115 prevents the broken portions 88A from coming in contact with the elastic member 53. Thus, the risk of damaging the elastic member 53 can be prevented.

In the meantime, in the above-described embodiment and modifications, a normal to the planar portion 24B, on which the illumination window 41 and observation window 42 are provided, is set in such a state as to be substantially perpendicular to the longitudinal axis L. However, the direction of the normal to the planar portion 24B may properly be set.

In the above-described embodiment and modifications, the example was described in which the distal structure portion 24 is of a side-viewing type. However, needless to say, the distal structure portion 24 may be formed as a so-called forward-viewing type for observation in a direction along the longitudinal axis L of the insertion section 21, or may be formed as a so-called oblique-viewing type for observation in an arbitrary direction in a range between the direction along the longitudinal axis L of the insertion section and the direction perpendicular to the longitudinal axis L.

Although some embodiments were concretely described above with reference to the accompanying drawings, the present invention is not limited to the above embodiments, and includes any of embodiments which are implemented without departing from the spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
    an insertion section configured to be inserted into a lumen cavity along a longitudinal axis, a distal structure portion being provided at a distal end of the insertion section;
    a pivot base configured to pivotally move a treatment instrument at the distal structure portion;
    an elongated wire connected to the pivot base in the distal structure portion, the elongated wire being configured to remotely operate the pivot base;
    a flexible tube configured to cover the elongated wire water-tightly at the distal structure portion;
    a cover configured to be attached to the distal structure portion, the cover including an opening in a peripheral surface thereof;
    a cover removing tool configured to push an edge of the opening, in a state in which the cover removing tool is engaged with the cover; and
    a projection provided on the cover removing tool, the projection being configured to come in contact with the edge of the opening at a position apart from a position of a distal end of the tube in a direction of the longitudinal axis, in a state in which the cover removing tool is engaged with the cover.

2. The endoscope system of claim 1, wherein the projection is provided at a position apart from the distal end of the tube in the direction of the longitudinal axis, in a state in which the pivot base is located on a distal-most direction side of the direction of the longitudinal axis.

3. The endoscope system of claim 1, wherein the pivot base is exposed from the opening when the pivot base pivotally moves the treatment instrument.

4. The endoscope system of claim 1, wherein the cover includes:
    an annular portion, and
    a fragile portion provided on the annular portion such that at least a part of the fragile portion faces the opening, the fragile portion having a lower strength than a non-fragile portion of the annular portion.

5. The endoscope system of claim 4, wherein a position of the other end of the tube, which is located on an opposite side to the distal end of the tube, is provided at a position apart from a broken portion of the fragile portion in the direction of the longitudinal axis.

6. The endoscope system of claim 1, wherein the projection is configured to push the edge of the opening when the cover removing tool is rotated about a center axis thereof.

7. The endoscope system of claim 1, wherein a distal end of the tube is water-tightly connected to a distal side of the elongated wire or the pivot base, and wherein a proximal end of the tube is water-tightly connected to the distal structure portion.

8. A cover removing tool used for an endoscope,
    the endoscope comprising:
        an insertion section configured to be inserted into a lumen cavity along a longitudinal axis, a distal structure portion being provided at a distal end of the insertion section;
        a pivot base configured to pivotally move a treatment instrument at the distal structure portion;
        an elongated wire connected to the pivot base in the distal structure portion, the elongated wire being configured to remotely operate the pivot base;
        a flexible tube configured to cover the elongated wire water-tightly at the distal structure portion; and
        a cover configured to be attached to the distal structure portion, the cover including an opening in a peripheral surface thereof,
    the cover removing tool comprising:
        a working portion configured to cover at least a portion of a distal-most end of the cover, and
        a projection configured to project from an internal surface of the working portion, the projection being configured to come in contact with the edge of the opening at a position apart from a position of a distal end of the tube in a direction of the longitudinal axis, in a state in which the cover removing tool is engaged with the distal-most end of the cover.

* * * * *